(12) United States Patent
Bokinsky et al.

(10) Patent No.: US 9,096,859 B2
(45) Date of Patent: Aug. 4, 2015

(54) MICROBIAL CONVERSION OF PLANT BIOMASS TO ADVANCED BIOFUELS

(75) Inventors: Gregory Bokinsky, Berkeley, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 279 days.

(21) Appl. No.: 13/357,566

(22) Filed: Jan. 24, 2012

(65) Prior Publication Data

US 2012/0190090 A1 Jul. 26, 2012

Related U.S. Application Data

(60) Provisional application No. 61/436,538, filed on Jan. 26, 2011.

(51) Int. Cl.
| | |
|---|---|
| *C12P 7/16* | (2006.01) |
| *C12N 9/00* | (2006.01) |
| *C12N 1/20* | (2006.01) |
| *C12N 15/00* | (2006.01) |
| *C07H 21/04* | (2006.01) |
| *C12N 15/52* | (2006.01) |
| *C12N 9/24* | (2006.01) |

(52) U.S. Cl.
CPC ............. *C12N 15/52* (2013.01); *C12N 9/248* (2013.01); *C12P 7/16* (2013.01); *C12P 2203/00* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 7,915,026 | B2 | 3/2011 | Keasling et al. |
| 7,985,567 | B2 | 7/2011 | Chou et al. |
| 2009/0311755 | A1* | 12/2009 | Harris et al. ............. 435/106 |
| 2010/0129885 | A1 | 5/2010 | Khramtsov et al. |
| 2010/0170148 | A1 | 7/2010 | Steen et al. |
| 2010/0242345 | A1 | 9/2010 | Keasling et al. |
| 2010/0261241 | A1 | 10/2010 | Khramtsov et al. |
| 2011/0021790 | A1 | 1/2011 | Katz et al. |
| 2011/0072714 | A1 | 3/2011 | Gaertner |
| 2011/0097769 | A1 | 4/2011 | Del Cardayre et al. |

FOREIGN PATENT DOCUMENTS

| | | |
|---|---|---|
| EP | 2194120 | 6/2010 |
| WO | WO-2007/136762 | 11/2007 |
| WO | WO-2008/100251 | 8/2008 |
| WO | WO-2008/113041 | 9/2008 |
| WO | WO-2009/132008 | 10/2009 |
| WO | WO-2010/127318 | 11/2010 |
| WO | WO-2011/011796 | 1/2011 |
| WO | WO-2011/044279 | 4/2011 |
| WO | WO-2011/153516 | 12/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Sillers et al. Biotechnol Bioeng. Jan. 1, 2009;102(1):38-49.*
Qian et al. Biotechnol Bioeng. Oct. 15, 2008;101(3):587-601.*
Deboy et al. J Bacteriol. Aug. 2008;190(15):5455-63. Epub Jun. 13, 2008.*
Cardinale et al., "Contextualizing Context for Synthetic Biology—Identifying Causes of Failure of Synthetic Biological Systems", Biotechnology Journal, vol. 7, 2012, pp. 856-866.
Fortman et al., "Biofuel Alternatives to Ethanol: Pumping the Microbial Well", Trends in Biotechnology, vol. 26, No. 7, 2008, pp. 375-381.
Keasling, Jay D., "Manufacturing Molecules Through Metabolic Engineering", Science, vol. 330, Dec. 3, 2010, pp. 1355-1358.
La Grange et al., "Engineering Cellulolytic Ability into Bioprocessing Organisms", Appl. Microbiol. Biotechnol., vol. 87, 2010, pp. 1195-1208.
Lynd et al., "Consolidated Bioprocessing of Cellulosic Biomass: An Update", Current Opinion in Biotechnology, vol. 16, 2005, pp. 577-583.
Steen et al., "Microbial Production of Fatty-Acid-Derived Fuels and Chemicals from Plant Biomass", Nature, vol. 463, Jan. 28, 2010, pp. 559-563.

* cited by examiner

*Primary Examiner* — Christian Fronda
(74) *Attorney, Agent, or Firm* — Morrison & Foerster LLP

(57) ABSTRACT

The invention provides consolidated bioprocessing methods and host cells. The host cells are capable of directly converting biomass polymers or sunlight into alcohols or branched-chain hydrocarbons. In particular, the invention provides a method for producing alcohols or branched-chain hydrocarbons from a biomass polymer, including providing a genetically engineered host cell, culturing the host cell in a medium containing a biomass polymer as a carbon source such that recombinant nucleic acids in the cell are expressed, and extracting alcohols or branched-chain hydrocarbons from the culture.

13 Claims, 15 Drawing Sheets
(6 of 15 Drawing Sheet(s) Filed in Color)

MICROBIAL CONVERSION OF PLANT BIOMASS TO ADVANCED BIOFUELS

CROSS-REFERENCE TO RELATED APPLICATIONS

This application claims the benefit of U.S. Provisional Application No. 61/436,538, filed Jan. 26, 2011, which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 4162720093SEQLISTING.txt, date recorded: Jan. 24, 2012, size: 25 KB).

FIELD OF THE INVENTION

The present disclosure relates to methods and compositions for the production of advanced biofuels from plant biomass.

BACKGROUND OF THE INVENTION

The conversion of plant biomass into biofuels by engineered microbes would allow the replacement of petroleum-derived fuels with a renewable and $CO_2$-neutral source of liquid fuels (National Research Council (U.S.), Panel on Alternative Liquid Transportation Fuels, *Liquid transportation fuels from coal and biomass: technological status, costs, and environmental impacts* (National Academies Press, Washington, D.C., 2009), pp. xvii, 370 p.)). Significant advances in metabolic engineering have enabled the production of compounds that are fully compatible with existing engines and fuel transport infrastructure (J. L. Fortman et al., Trends in Biotechnology 26, 375 (July 2008); J. D. Keasling, Science 330, 1355 (Dec. 3, 2010)). Production of biofuels from abundant materials, such as lignocellulosic plant biomass and cellulosic waste, avoids many of the problems associated with current grain-based feedstocks, and could slow anthropogenic $CO_2$ increases, provided the biomass is responsibly grown and harvested (D. Tilman et al., Science 325, 270 (Jul. 17, 2009)).

Unfortunately, lignocellulose is not yet an economically viable feedstock, in part because substantial amounts of hydrolase enzymes are needed to convert it into fermentable sugars in high yields. These enzymes are typically generated in a dedicated process, either at the biorefinery or offsite, incurring substantial capital and material expenses (National Research Council (U.S.), Panel on Alternative Liquid Transportation Fuels, *Liquid transportation fuels from coal and biomass: technological status, costs, and environmental impacts* (National Academies Press, Washington, D.C., 2009), pp. xvii, 370 p.)). An alternative approach, known as consolidated bioprocessing, avoids these costs by combining enzyme generation, biomass hydrolysis, and fuel production into a single process step (L. R. Lynd, P. J. Weimer, W. H. van Zyl, I. S. Pretorius, Microbiol Mol Biol Rev 66, 506 (September 2002); L. R. Lynd, W. H. van Zyl, J. E. McBride, M. Laser, Curr Opin Biotechnol 16, 577 (October 2005)) (FIG. 1A). This can be achieved either by using a consortium of microbes with biomass-degrading and biofuel-producing capabilities (T. S. Bayer et al., Journal of the American Chemical Society 131, 6508 (May 13, 2009)), or by engineering both capabilities into a single organism. There have been demonstrations of engineered yeast or bacterial species fermenting various highly refined cellulosic substrates directly into ethanol or converting a model hemicellulose substrate into biodiesel (L. R. Lynd, W. H. van Zyl, J. E. McBride, M. Laser, Curr Opin Biotechnol 16, 577 (October 2005); D. C. la Grange, R. den Haan, W. H. van Zyl, Applied Microbiology and Biotechnology 87, 1195 (July 2010); E. J. Steen et al., Nature 463, 559 (Jan. 28, 2010)). However, no organism capable of converting an unrefined plant feedstock into biofuels that have the combustion properties of petrochemical fuels has yet been reported.

Thus, a need exists for a consolidated bioprocess in which cells produce advanced biofuels directly from an input of biomass without the addition of exogenous substrates or enzymes.

BRIEF SUMMARY OF THE INVENTION

Described herein are consolidated bioprocessing methods and host cells. The host cells are capable of producing alcohols or branched-chain hydrocarbons. In certain embodiments, the host cells have the ability to degrade plant biomass and utilize it as a sole carbon source for production of alcohols or branched-chain hydrocarbons.

Thus, one aspect includes a method for producing butanol from a biomass polymer, including the steps of providing a host cell, where the host cell contains one or more recombinant nucleic acids encoding a crotonase, a butyryl-coA dehydrogenase, an electron transport flavoprotein B, an electron transport flavoprotein A, a 3-hydroxybutyryl-coA dehydrogenase, an acetyl-coA acetyltransferase, or an aldehyde/alcohol dehydrogenase, and one or more biomass polymer-degrading enzymes, where at least one of the one or more biomass polymer-degrading enzymes is secreted from the host cell, culturing the host cell in a medium to form a culture such that the one or more recombinant nucleic acids are expressed in the cell, where the medium comprises a biomass polymer as a carbon source for the host cell, and extracting butanol from the culture.

In certain embodiments, the host cell contains an endogenous nucleic acid encoding an alcohol dehydrogenase. In certain embodiments, the host cell is modified such that expression of the alcohol dehydrogenase is attenuated relative to the level of expression in a non-modified cell. In certain embodiments, the host cell is selected from a bacterial cell, a fungal cell, a yeast cell, a plant cell, an animal, and a human cell. In certain embodiments, the host cell is a bacterial cell. In certain embodiments, the bacterial cell is an *E. coli* cell. In certain embodiments, the host cell is a fungal cell. In certain embodiments, the fungal cell is a yeast cell. In certain embodiments, the host cell is a plant, animal, or human cell. In certain embodiments, the crotonase is crt from *C. acetylbutylicum*, the butyryl-coA dehydrogenase is bcd from *C. acetylbutylicum*, the electron transport flavoprotein B is etfB from *C. acetylbutylicum*, the electron transport flavoprotein A is etfA from *C. acetylbutylicum*, the 3-hydroxybutyryl-coA dehydrogenase is hbd from *C. acetylbutylicum*, the acetyl-coA acetyltransferase is atoB from *E. coli*, and the aldehyde/alcohol dehydrogenase is adhE2 from *C. acetylbutylicum*. In certain embodiments, the crotonase is crt from *C. acetylbutylicum*. In certain embodiments, the butyryl-coA dehydrogenase is bcd from *C. acetylbutylicum*. In certain embodiments, the electron transport flavoprotein B is etfB from *C. acetylbutylicum*. In certain embodiments, the electron transport flavoprotein A is etfA from *C. acetylbutylicum*. In certain embodiments, the 3-hydroxybutyryl-coA dehydrogenase is hbd from *C. acetylbutylicum*. In certain embodiments, the acetyl-coA acetyltransferase is atoB from *E. coli*. In certain embodiments, the aldehyde/alcohol dehydrogenase is adhE2 from *C. acetylbutylicum*. In certain embodiments, the biomass polymer is cellulose. In certain embodiments, the one or more biomass polymer-degrading enzymes are a cellulase and a β-glucosidase. In certain embodiments, the cellulase is cel from *Bacillus* sp. D04. In certain embodiments, the β-glucosidase is selected from the group consisting of cel3A and cel3B from *Cellvibrio japonicus*. In certain embodiments, the biomass polymer is hemicellulose. In certain embodiments, the hemicellulose is xylan. In certain embodiments, the one or more biomass polymer-degrading enzymes are an endoxylanase and a xylobiosidase. In certain embodiments, the endoxylanase is xyn10B from *Clostridium stercorarium*. In certain embodiments, the xylobiosidase is gly43F from *Cellvibrio japonicus*.

Another aspect includes a genetically modified host cell, containing one or more recombinant nucleic acids encoding a crotonase, a butyryl-coA dehydrogenase, an electron transport flavoprotein B, an electron transport flavoprotein A, a 3-hydroxybutyryl-coA dehydrogenase, an acetyl-coA acetyltransferase, or an aldehyde/alcohol dehydrogenase, and one or more biomass polymer-degrading enzymes, where at least one of the one or more biomass polymer-degrading enzymes is a secretory enzyme.

In certain embodiments, the host cell contains an endogenous nucleic acid encoding an alcohol dehydrogenase. In certain embodiments, the host cell is modified such that expression of the alcohol dehydrogenase is attenuated relative to the level of expression in a non-modified cell. In certain embodiments, the host cell is selected from a bacterial cell, a fungal cell, a yeast cell, a plant cell, an animal cell, and a human cell. In certain embodiments, the host cell is a bacterial cell. In certain embodiments, the bacterial cell is an *E. coli* cell. In certain embodiments, the host cell is a fungal cell. In certain embodiments, the fungal cell is a yeast cell. In certain embodiments, the host cell is a plant, animal, or human cell. In certain embodiments, the crotonase is crt from *C. acetylbutylicum*, the butyryl-coA dehydrogenase is bcd from *C. acetylbutylicum*, the electron transport flavoprotein B is etfB from *C. acetylbutylicum*, the electron transport flavoprotein A is etfA from *C. acetylbutylicum*, the 3-hydroxybutyryl-coA dehydrogenase is hbd from *C. acetylbutylicum*, the acetyl-coA acetyltransferase is atoB from *E. coli*, and the aldehyde/alcohol dehydrogenase is adhE2 from *C. acetylbutylicum*. In certain embodiments, the crotonase is crt from *C. acetylbutylicum*. In certain embodiments, the butyryl-coA dehydrogenase is bcd from *C. acetylbutylicum*. In certain embodiments, the electron transport flavoprotein B is etfB from *C. acetylbutylicum*. In certain embodiments, the electron transport flavoprotein A is etfA from *C. acetylbutylicum*. In certain embodiments, the 3-hydroxybutyryl-coA dehydrogenase is hbd from *C. acetylbutylicum*. In certain embodiments, the acetyl-coA acetyltransferase is atoB from *E. coli*. In certain embodiments, the aldehyde/alcohol dehydrogenase is adhE2 from *C. acetylbutylicum*. In certain embodiments, the host cell further contains a recombinant nucleic acid encoding a naturally secreted protein, where the secreted protein is fused to at least one of the one or more biomass polymer-degrading enzymes. In certain embodiments, the naturally secreted protein is OsmY from *E. coli*. In certain embodiments, the one or more biomass polymer-degrading enzymes are a cellulase and a β-glucosidase. In certain embodiments, the cellulase is cel from *Bacillus* sp. D04. In certain embodiments, the (3-glucosidase is selected from the group consisting of cel3A and cel3B from *Cellvibrio japonicus*. In certain embodiments, the one or more biomass polymer-degrading enzymes are an endoxylanase and a xylobiosidase. In certain embodiments, the endoxylanase is xyn10B from *Clostridium stercorarium*. In certain embodiments, the xylobiosidase is gly43F from *Cellvibrio japonicus*.

Another aspect includes a method for producing pinene from a biomass polymer, including the steps of providing a host cell, where the host cell comprises one or more recombinant nucleic acids encoding a hydroxymethylglutaryl-coA synthase, a hydroxymethylglutaryl-coA reductase, a mevalonate kinase, a phosphomevalonate kinase, a phosphomevalonate decarboxylase, an isopentenyl pyrophosphate isomerase, a pinene synthase, a geranyl pyrophosphate synthase, or an acetyl-coA acetyltransferase, and one or more biomass polymer-degrading enzymes, where at least one of the one or more biomass polymer-degrading enzymes is secreted from the host cell, culturing the host cell in a medium to form a culture such that the one or more recombinant nucleic acids are expressed in the cell, where the medium comprises a biomass polymer as a carbon source for the host cell, and extracting pinene from the culture. In certain embodiments, the host cell is a bacterial cell. In certain embodiments, the bacterial cell is an *E. coli* cell. In certain embodiments, the host cell is a fungal cell. In certain embodiments, the fungal cell is a yeast cell. In certain embodiments, the host cell is a plant, animal, or human cell. In certain embodiments, the hydroxymethylglutaryl-coA synthase is HMGS from *S. cerevisiae*. In certain embodiments, the hydroxymethylglutaryl-coA reductase dehydrogenase is HMGR from *S. cerevisiae*. In certain embodiments, the mevalonate kinase is MK from *S. cerevisiae*. In certain embodiments, the phosphomevalonate kinase is PMK from *S. cerevisiae*. In certain embodiments, the phosphomevalonate decarboxylase is PMD from *S. cerevisiae*. In certain embodiments, the isopentenyl pyrophosphate isomerase is idi from *E. coli*. In certain embodiments, the pinene synthase is PINE from *P. taeda*. In certain embodiments, the geranyl pyrophosphate synthase is GPPS from *A. grandis*. In certain embodiments, the acetyl-coA acetyltransferase is atoB from *E. coli*. In certain embodiments, the biomass polymer is cellulose. In certain embodiments, the one or more biomass polymer-degrading enzymes are a cellulase and a β-glucosidase. In certain embodiments, the cellulase is cel from *Bacillus* sp. D04. In certain embodiments, the β-glucosidase is selected from the group consisting of cel3A and cel3B from *Cellvibrio japonicus*. In certain embodiments, the biomass polymer is hemicellulose. In certain embodiments, the hemicellulose is xylan. In certain embodiments, the one or more biomass polymer-degrading enzymes are an endoxylanase and a xylobiosidase. In certain embodiments, the endoxylanase is xyn10B from *Clostridium stercorarium*. In certain embodiments, the xylobiosidase is gly43F from *Cellvibrio japonicus*.

Another aspect includes a genetically modified host cell, containing one or more recombinant nucleic acids encoding a hydroxymethylglutaryl-coA synthase, a hydroxymethylglutaryl-coA reductase, a mevalonate kinase, a phosphomevalonate kinase, a phosphomevalonate decarboxylase, an isopentenyl pyrophosphate isomerase, a pinene synthase, a geranyl pyrophosphate synthase, or an acetyl-coA acetyltransferase, and one or more biomass polymer-degrading enzymes, where at least one of the one or more biomass polymer-degrading enzymes is a secretory enzyme. In certain embodiments, the host cell is a bacterial cell. In certain embodiments, the bacterial cell is an *E. coli* cell. In certain embodiments, the host cell is a fungal cell. In certain embodiments, the fungal cell is a yeast cell. In certain embodiments, the host cell is a plant, animal, or human cell. In certain embodiments, the hydroxymethylglutaryl-coA synthase is HMGS from *S. cerevisiae*. In certain embodiments, the hydroxymethylglutaryl-coA reductase is HMGR from *S. cerevisiae*. In certain embodiments, the mevalonate kinase is MK from *S. cerevisiae*. In certain embodiments, the phosphomevalonate kinase is PMK from *S. cerevisiae*. In certain embodiments, the phosphomevalonate decarboxylase is PMD from *S. cerevisiae*. In certain embodiments, the isopentenyl pyrophosphate isomerase is idi from *E. coli*. In certain embodiments, the pinene synthase is PINE from *P. taeda*. In certain embodiments, the geranyl pyrophosphate synthase is GPPS from *A. grandis*. In certain embodiments, the acetyl-coA acetyltransferase is atoB from *E. coli*. In certain embodiments, the host cell further contains a recombinant nucleic acid encoding a naturally secreted protein, where the secreted protein is fused to at least one of the one or more biomass polymer-degrading enzymes. In certain embodiments, the naturally secreted protein is OsmY from *E. coli*. In certain embodiments, the one or more biomass polymer-degrading enzymes are a cellulase and a β-glucosidase. In certain embodiments, the cellulase is cel from *Bacillus* sp. D04. In certain embodiments, the β-glucosidase is selected from the group consisting of cel3A and cel3B from *Cellvibrio japonicus*. In certain embodiments, the one or more biomass polymer-degrading enzymes are an endoxylanase and a xylobiosidase. In certain embodiments, the endoxylanase is xyn10B from *Clostridium stercorarium*. In certain embodiments, the xylobiosidase is gly43F from *Cellvibrio japonicus*.

In another aspect, the invention includes methods of producing alcohols or branched-chain hydrocarbons from sunlight. In one embodiment, an organism capable of using sunlight as a carbon source is genetically engineered to contain the enzymatic pathways necessary to produce alcohols or branched-chain hydrocarbons as described above in other aspects of the invention. In another embodiment, the host cells of the above aspects of the invention are further genetically engineered to contain enzymatic pathways that allow the host cell to utilize sunlight as a carbon source and to produce alcohols or branched-chain hydrocarbons directly from sunlight.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF THE INVENTION

Figure 1:
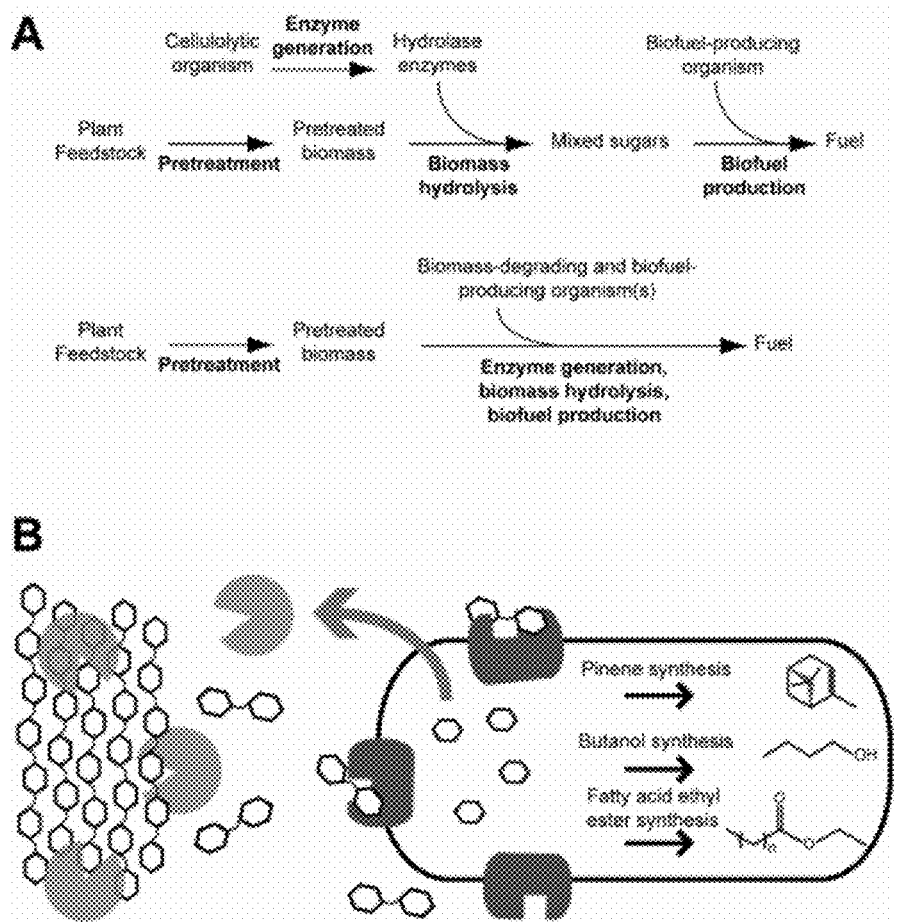
FIG. 1 shows consolidated bioprocessing of plant biomass into biofuels by *E. coli*. Part A shows two processes for biofuel production. Typically, cellulase and hemicellulase enzymes are produced in a process step separate from biomass hydrolysis and biofuel production (top). Consolidated bioprocessing (bottom) combines enzyme generation, biomass hydrolysis, and biofuel production into a single stage. Part B shows a method of engineering *E. coli* for use in consolidated bioprocessing. Cellulose and hemicellulose are hydrolyzed by secreted cellulase and hemicellulose enzymes into soluble oligosaccharides. β-glucosidase enzymes further hydrolyze the oligosaccharides into monosaccharides, which are metabolized into biofuels via heterologous pathways.

The present disclosure relates to consolidated bioprocessing methods and host cells. In certain embodiments, the host cells are capable of producing alcohols and branched-chain hydrocarbons. In other embodiments, the host cells have the ability to directly convert biomass polymers or sunlight into alcohols and branched-chain hydrocarbons. In one aspect, the invention provides a method for producing alcohols and branched-chain hydrocarbons from a biomass polymer including providing a genetically engineered host cell, culturing the host cell in a medium containing a carbon source such that recombinant nucleic acids in the cell are expressed, and extracting alcohols and branched-chain hydrocarbons from the culture.

Host Cells of the Invention

"Host cell" and "host microorganism" are used interchangeably herein to refer to a living biological cell that can be transformed via insertion of recombinant DNA or RNA. Such recombinant DNA or RNA can be in an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

Any prokaryotic or eukaryotic host cell may be used in the present invention so long as it remains viable after being transformed with a sequence of nucleic acids. In preferred embodiments, the host microorganism is bacterial, and in some embodiments, the bacteria are *E. coli*. In other embodiments, the bacteria are cyanobacteria. Additional examples of bacterial host cells include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis,* and *Paracoccus* taxonomical classes. Preferably, the host cell is not adversely affected by the transduction of the necessary nucleic acid sequences, the subsequent expression of the proteins (e.g., enzymes), or the resulting intermediates.

Suitable eukaryotic cells include, but are not limited to, fungal, plant, insect or mammalian cells. Suitable fungal cells are yeast cells, such as yeast cells of the *Saccharomyces* genus. In some embodiments the eukaryotic cell is from algae, e.g., *Chlamydomonas reinhardtii, Scenedesmus obliquus, Chlorella vulgaris,* or *Dunaliella salina*.

The host cells of the present invention are genetically modified in that recombinant nucleic acids have been introduced into the host cells, and as such the genetically modified host cells do not occur in nature. The suitable host cell is one capable of expressing one or more nucleic acid constructs encoding one or more enzymes capable of catalyzing a desired biosynthetic reaction, In preferred embodiments, the one or more enzymes include, but are not limited to a crotonase, a butyryl-coA dehydrogenase, an electron transport flavoprotein B, an electron transport flavoprotein A, a 3-hydroxybutyryl-coA dehydrogenase, an acetyl-coA acetyltransferase, or an aldehyde/alcohol dehydrogenase, one or more biomass polymer-degrading enzymes, a hydroxymethylglutaryl-coA synthase, a hydroxymethylglutaryl-coA reductase, a mevalonate kinase, a phosphomevalonate kinase, a phosphomevalonate decarboxylase, an isopentenyl pyrophosphate isomerase, a pinene synthase, and a geranyl pyrophosphate synthase. In preferred embodiments, the one or more enzymes are capable of catalyzing reactions which lead to the production of alcohols and branched-chain hydrocarbons.

"Recombinant nucleic acid" or "heterologous nucleic acid" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but is present in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid. Specifically, the present invention describes the introduction of an expression vector into a host cell, wherein the expression vector contains a nucleic acid sequence coding for an enzyme that is not normally found in a host cell or contains a nucleic acid coding for an enzyme that is normally found in a cell but is under the control of different regulatory sequences. With reference to the host cell's genome, then, the nucleic acid sequence that codes for the enzyme is recombinant.

As used herein, a "peptide" and a "polypeptide" are amino acid sequences including a plurality of consecutive polymerized amino acid residues. Typically, peptides are those molecules including up to 50 amino acid residues, and polypeptides include more than 50 amino acid residues. The peptide or polypeptide may include modified amino acid residues, naturally occurring amino acid residues not encoded by a codon, and non-naturally occurring amino acid residues. As used herein, "protein" may refer to a peptide or a polypeptide of any size.

In some embodiments, the host cell naturally produces any of the precursors for the production of the alcohols or branched-chain hydrocarbons. These genes encoding the desired enzymes may be heterologous to the host cell, or these genes may be endogenous to the host cell but are operatively linked to heterologous promoters and/or control regions which result in higher expression of the gene(s) in the host cell. In other embodiments, the host cell does not naturally produce the desired alcohol or branched-chain hydrocarbon and comprises heterologous nucleic acid constructs capable of expressing one or more genes necessary for producing those molecules.

"Endogenous" as used herein with reference to a nucleic acid molecule or polypeptide and a particular cell or microorganism refers to a nucleic acid molecule or polypeptide that is in the cell and was not introduced into the cell using recombinant engineering techniques, for example, a gene that was present in the cell when the cell was originally isolated from nature.

Each of the desired enzymes capable of catalyzing the desired reaction can be endogenous or heterologous to the host cell. Where the enzyme is endogenous to the host cell, the host cell may be genetically modified to modulate expression of the enzyme. This modification can involve the modification of the chromosomal gene encoding the enzyme in the host cell or introduction of a nucleic acid construct encoding the gene of the enzyme into the host cell. One of the effects of the modification is that expression of the enzyme is modulated in the host cell, such as increased expression of the enzyme in the host cell as compared to expression of the enzyme in an unmodified host cell. Alternatively, modification of expression of an enzyme may result in decreased expression of the enzyme in the host cell as compared to expression of the enzyme in an unmodified cell. For example, a host cell may contain an endogenous nucleic acid that encodes an alcohol dehydrogenase. In some aspects of the invention, the host cell may be genetically modified such that expression of the alcohol dehydrogenase is reduced or attenuated relative to its level of expression in an unmodified host cell.

Genetic modifications include any type of modification and specifically include modifications made by recombinant technology and/or by classical mutagenesis. As used herein, genetic modifications that result in a decrease in gene expression, in the function of the gene, or in the function of the gene product (i.e., the protein encoded by the gene) can be referred to as inactivation (complete or partial), deletion, interruption, blockage, silencing, or down-regulation, or attenuation of expression of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). More specifically, reference to decreasing the action or activity of enzymes discussed herein generally refers to any genetic modification in the microorganism in question which results in decreased expression and/or functionality (biological activity) of the enzymes and includes decreased activity of the enzymes (e.g., specific activity), increased inhibition or degradation of the enzymes, as well as a reduction or elimination of expression of the enzymes. For example, the action or activity of an enzyme of the present invention can be decreased by blocking or reducing the production of the enzyme, reducing enzyme activity, or inhibiting the activity of the enzyme. Combinations of some of these modifications are also possible. Blocking or reducing the production of an enzyme can include placing the gene encoding the enzyme under the control of a promoter that requires the presence of an inducing compound in the growth medium. By establishing conditions such that the inducer becomes depleted from the medium, the expression of the gene encoding the enzyme (and therefore, enzyme synthesis) could be turned off. Blocking or reducing the activity of an enzyme could also include using an excision technology approach similar to that described in U.S. Pat. No. 4,743,546. To use this approach, the gene encoding the enzyme of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

"Genetically engineered" or "genetically modified" refers to any host cell modified by any recombinant DNA or RNA technology. In other words, the host cell has been transfected, transformed, or transduced with a recombinant polynucleotide molecule, and thereby been altered so as to cause the cell to alter expression of a desired protein. Methods and vectors for genetically engineering host cells are well known in the art; for example, various techniques are illustrated in *Current Protocols in Molecular Biology*, Ausubel et al., eds. (Wiley &

Sons, New York, 1988, and quarterly updates). Genetic engineering techniques include but are not limited to expression vectors, targeted homologous recombination, and gene activation (see, for example, U.S. Pat. No. 5,272,071), and transactivation by engineered transcription factors (see, for example, Segal et al., 1999, *Proc Natl Acad Sci USA* 96(6): 2758-63).

Genetic modifications that result in an increase in gene expression or function can be referred to as amplification, overproduction, overexpression, activation, enhancement, addition, or up-regulation of a gene. More specifically, reference to increasing the action (or activity) of enzymes or other proteins discussed herein generally refers to any genetic modification in the microorganism in question that results in increased expression and/or functionality (biological activity) of the enzymes or proteins and includes higher activity of the enzymes (e.g., specific activity or in vivo enzymatic activity), reduced inhibition or degradation of the enzymes, and overexpression of the enzymes. For example, gene copy number can be increased, expression levels can be increased by use of a promoter that gives higher levels of expression than that of the native promoter, or a gene can be altered by genetic engineering or classical mutagenesis to increase the biological activity of an enzyme. Combinations of some of these modifications are also possible.

In general, according to the present invention, an increase or a decrease in a given characteristic of a mutant or modified enzyme (e.g., enzyme activity) is made with reference to the same characteristic of a wild-type (i.e., normal, not modified) enzyme that is derived from the same organism (i.e., from the same source or parent sequence), and is measured or established under the same or equivalent conditions. Similarly, an increase or decrease in a characteristic of a genetically modified microorganism (e.g., expression and/or biological activity of a protein, or production of a product) is made with reference to the same characteristic of a wild-type microorganism of the same species, and preferably the same strain, under the same or equivalent conditions. Such conditions include the assay or culture conditions (e.g., medium components, temperature, pH, etc.) under which the activity of the protein (e.g., expression or biological activity) or other characteristic of the microorganism is measured, as well as the type of assay used, the host microorganism that is evaluated, etc. As discussed above, equivalent conditions are conditions (e.g., culture conditions) which are similar, but not necessarily identical (e.g., some conservative changes in conditions can be tolerated), and which do not substantially change the effect on microbe growth or enzyme expression or biological activity as compared to a comparison made under the same conditions.

Preferably, a genetically modified host cell that has a genetic modification that increases or decreases the activity of a given protein (e.g., an enzyme) has an increase or decrease, respectively, in the activity (e.g., expression, production and/or biological activity) of the protein, as compared to the activity of the wild-type protein in a wild-type microorganism, of at least about 5%, and more preferably at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, or any percentage, in whole integers between 5% and 100% (e.g., 6%, 7%, 8%, etc.). The same differences are preferred when comparing the activity of an isolated modified nucleic acid molecule or protein directly to the activity of an isolated wild-type nucleic acid molecule or protein (e.g., if the comparison is done in vitro as compared to in vivo).

In another aspect of the invention, a genetically modified host cell that has a genetic modification that increases or decreases the activity of a given protein (e.g., an enzyme) has an increase or decrease, respectively, in the activity (e.g., expression, production and/or biological activity) of the protein, as compared to the activity of the wild-type protein in a wild-type microorganism, of at least about 2-fold, and more preferably at least about 5-fold, and more preferably at least about 10-fold, and more preferably about 20-fold, and more preferably at least about 30-fold, and more preferably at least about 40-fold, and more preferably at least about 50-fold, and more preferably at least about 75-fold, and more preferably at least about 100-fold, and more preferably at least about 125-fold, and more preferably at least about 150-fold, or any whole integer increment starting from at least about 2-fold (e.g., 3-fold, 4-fold, 5-fold, 6-fold, etc.).

Enzymes and Constructs Encoding Thereof of the Invention

Enzymes of the invention include any enzymes involved in pathways that lead directly or indirectly to the production of alcohols and branched-chain hydrocarbons in a host cell. Enzymes of the invention may, for example, catalyze the production of intermediates or substrates for further reactions leading to the production of alcohols and branched-chain hydrocarbons in a host cell. In some embodiments, enzymes of the invention are secretory enzymes, i.e., are secreted from the host cell. Enzymes of the invention include, without limitation, a crotonase, a butyryl-coA dehydrogenase, an electron transport flavoprotein B, an electron transport flavoprotein A, a 3-hydroxybutyryl-coA dehydrogenase, an acetyl-coA acetyltransferase, or an aldehyde/alcohol dehydrogenase, one or more biomass polymer-degrading enzymes, a hydroxymethylglutaryl-coA synthase, a hydroxymethylglutaryl-coA reductase, a mevalonate kinase, a phosphomevalonate kinase, a phosphomevalonate decarboxylase, an isopentenyl pyrophosphate isomerase, a pinene synthase, and a geranyl pyrophosphate synthase.

A crotonase includes any enzyme that stabilizes an enolate anion intermediate derived from an acyl-CoA substrate. For example, a crotonase may be crt from *C. acetylbutylicum* (see Table 10) or similar proteins from *Clostridium perfringens* (NCBI NP_561011.1) or *Thermoanaerobacterium thermosaccharolyticum* (Genbank ID CAB07495.1).

A butyryl-coA dehydrogenase includes any flavoprotein that acts upon butyryl-coenzyme A. For example, a butyryl-coA dehydrogenase may be bcd from *C. acetylbutylicum* (see Table 10) or similar proteins from *Bacillus cereus* (NCBI YP_086611.1) or *Meiothermus silvanus* (NCBI YP_003685662.1).

Electron transport flavoproteins A and B include any protein that serves as a specific electron acceptor for several dehydrogenases, including five acyl-CoA dehydrogenases, glutaryl-CoA and sarcosine dehydrogenase. The protein transfers the electrons to the main mitochondrial respiratory chain via ETF-ubiquinone oxidoreductase (ETF dehydrogenase). For example, the electron transport flavoproteins A and B may be the etfA and etfB from *C. acetylbutylicum* (see Table 10) or similar proteins from *Clostridium carboxidivorans*

(NCBI ADO12112.1 and ADO12111.1) or *Peptostreptococcus anaerobius* (NCBI ZP_06425252.1 and ZP_06425210.1).

A 3-hydroxybutyryl-coA dehydrogenase includes any enzyme that that catalyzes the chemical reaction (S)-3-hydroxybutanoyl-CoA+NADP$^+$ ↔ 3-acetoacetyl-CoA+ NADPH+H$^+$. Other names in common use include beta-hydroxybutyryl coenzyme A dehydrogenase, L(+)-3-hydroxybutyryl-CoA dehydrogenase, BHBD, dehydrogenase, L-3-hydroxybutyryl coenzyme A (nicotinamide adenine, dinucleotide phosphate), L-(+)-3-hydroxybutyryl-CoA dehydrogenase, and beta-hydroxybutyryl-CoA dehydrogenase. For example, a 3-hydroxybutyryl-coA dehydrogenase may be hbd from *C. acetylbutylicum* (see Table 10) or similar proteins from *Corynebacterium jeikeium* or *Cupriavidus metallidurans*.

An acetyl-coA acetyltransferase includes any enzyme that converts two units of acetyl-CoA to acetoacetyl CoA in the mevalonate pathway. This enzyme may also be called a thiolase. For example, an acetyl-coA acetyltransferase may be atoB from *E. coli* or similar proteins from *Mycobacterium vanbaalenii* (NCBI YP_951646.1) or *Syntrophobacter fumaroxidans* (NCBI YP_847688.1).

An aldehyde/alcohol dehydrogenase is any bifunctional enzyme that catalyzes both the oxidation (dehydrogenation) of aldehydes and the interconversion between alcohols and aldehydes and ketones with the reduction of NAD$^+$ to NADH. For example, an aldehyde/alcohol dehydrogenase may be adhE2 from *C. acetylbutylicum* (see Table 10) or similar proteins from *Kluyveromyces lactis* (NCBI CAG99938.1) or *Chloroflexus aurantiacus* (NCBI YP_001633676.1).

A hydroxymethylglutaryl-coA synthase is any enzyme that catalyzes the chemical reaction acetyl-CoA+H$_2$O+acetoacetyl-CoA ↔ (S)-3-hydroxy-3-methylglutaryl-CoA+ CoA. For example, a hydroxymethylglutaryl-coA synthase may be HMGS from *S. cerevisiae* (see Table 10) or similar proteins from *Enterococcus faecalis* (NCBI ZP_06632316.1) or *Vulcanisaeta distributa* (NCBI ADN51383.1).

A hydroxymethylglutaryl-coA reductase is any enzyme that catalyzes the reaction (R)-mevalonate+CoA+2 NADP$^+$ ↔ $^{(S)}$-3-hydroxy-3-methylglutaryl-CoA+2 NADPH+2 H$^+$. For example, a hydroxymethylglutaryl-coA reductase may be HMGR from *S. cerevisiae* (see Table 10) or similar proteins from *Catharanthus roseus* (NCBI AAA33108.1) or *Polaribacter irgensii* (NCBI ZP_01119141.1).

A mevalonate kinase is any enzyme that catalyzes the reaction ATP+(R)-mevalonate ↔ ADP+(R)-5-phosphomevalonate. For example, a mevalonate kinase may be MK from *S. cerevisiae* (see Table 10) or similar proteins from *Thermococcus gammatolerans* (NCBI YP_002960094.1) or *Methanothermus fervidus* (NCBI YP_004004455.1).

A phosphomevalonate kinase is any enzyme that catalyzes the conversion of mevalonate-5-phosphate to mevalonate-5-pyrophosphate. For example, a phosphomevalonate kinase may be PMK from *S. cerevisiae* (see Table 10) or similar proteins from *Staphylococcus aureus* (NCBI AAG02426.1) or *Bacillus coagulans* (NCBI ZP_04431080.1).

A phosphomevalonate decarboxylase is any enzyme that catalyzes the conversion of mevalonate-5-pyrophosphate to isopentenyl-5-pyrophosphate. For example, a phosphomevalonate decarboxylase may be PMD from *S. cerevisiae* (see Table 10) or similar proteins from *Methanobrevibacter ruminantium* (NCBI ADC46770.1) or *Lactobacillus brevis* (NCBI YP_795032).

An isopentenyl pyrophosphate isomerase is any enzyme that catalyzes the conversion of 3-isopentenyl pyrophosphate to dimethylallyl pyrophosphate. For example, an isopentenyl pyrophosphate isomerase may be idi from *E. coli* (see Table 10) or similar proteins from *Listeria monocytogenes* (NCBI NP_464908.1) or *Bacillus licheniformis* (NCBI YP_091997.1).

A pinene synthase is any enzyme that catalyzes the reaction geranyl diphosphate ↔ pinene+diphosphate. For example, a pinene synthase may be PINE from *P. taeda* (see Table 10) or similar proteins from *Picea sitchensis* (NCBI AAP72020.1) or *Quercus ilex* (NCBI CAK55186.1).

A geranyl pyrophosphate synthase is any enzyme that catalyzes the synthesis of geranyl pyrophosphate from isopentenyl pyrophosphate (IPP) and dimethylallyl pyrophosphate (DMAPP). For example, a geranyl pyrophosphate synthase may be GPPS from *A. grandis* (see Table 10) or similar enzymes from *Catharanthus roseus* (NCBI ACC77966.1) or *Leuconostoc gasicomitatum* (NCBI YP_003773170.1).

Biomass polymer-degrading enzymes include any enzymes able to degrade any biomass polymer. "A biomass polymer" as described herein is any polymer contained in biological material. The biological material may be living or dead. A biomass polymer includes, for example, cellulose, xylan, hemicellulose, lignin, mannan, and other materials commonly found in biomass. Non-limiting examples of sources of a biomass polymer include grasses (e.g., switchgrass, *Miscanthus*), rice hulls, bagasse, cotton, jute, eucalyptus, hemp, flax, bamboo, sisal, abaca, straw, leaves, grass clippings, corn stover, corn cobs, distillers grains, legume plants, sorghum, sugar cane, sugar beet pulp, wood chips, sawdust, and biomass crops (e.g., *Crambe*). Sources of a biomass polymer may be an unrefined plant feedstock (e.g., ionic liquid-treated plant biomass) or a refined biomass polymer (e.g., beechwood xylan or phosphoric acid swollen cellulose).

Biomass polymer-degrading enzymes may include, without limitation, a cellulase, such as cel from *Bacillus* sp. D04, a β-glucosidase, such as cel3A or cel3B from *Cellvibrio japonicus*, an endoxylanase, such as xyn10B from *Clostridium stercorarium*, or a xylobiosidase such as gly43F from *Cellvibrio japonicus*.

The enzymes described herein can be readily replaced using a homologous enzyme thereof. "Homologous enzyme" as used herein refers to an enzyme that has a polypeptide sequence that is at least 40%, at least 45%, at least 50%, at least 55%, at least 60%, at least 65%, at least 70%, at least 75%, at least 80%, at least 85%, at least 90%, at least 95% or at least 99% identical to any of the enzymes described in this specification or in a cited reference. Homologous enzymes retain amino acid residues that are recognized as conserved for the enzyme. Homologous enzymes may have non-conserved amino acid residues replaced or found to be of a different amino acid, or amino acid(s) inserted or deleted, as long as they do not affect or have insignificant effect on the enzymatic activity of the homologous enzyme. A homologous enzyme has an enzymatic activity that is essentially the same as the enzymatic activity of any one of the enzymes described in this specification or in a cited reference in that it will catalyze the same reaction. The specific activity of the enzyme may be increased or decreased. Homologous enzymes may be found in nature or be an engineered mutant thereof. The enzymes described herein can also be replaced by an isozyme, an enzyme that may differ in amino acid sequence but that catalyzes the same chemical reaction.

The nucleic acid constructs of the present invention include nucleic acid sequences encoding one or more of the subject enzymes. The nucleic acids of the present invention are operably linked to promoters and optional control sequences such that the subject enzymes are expressed in a host cell cultured under suitable conditions. The promoters and control sequences may be specific for each host cell species. In some embodiments, expression vectors comprise the nucleic acid constructs. Methods for designing and making nucleic acid constructs and expression vectors are well known to those skilled in the art.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521: 719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. "Expression vector" or "vector" refers to a compound and/or composition that transduces, transforms, or infects a host cell, thereby causing the cell to express nucleic acids and/or proteins other than those endogenous to the cell, or in a manner not naturally occurring in the cell. An expression vector contains a sequence of nucleic acids (ordinarily RNA or DNA) to be expressed by the host cell. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Preferred expression vectors are plasmids, particularly those with restriction sites that have been well-documented and that contain the operational elements preferred or required for transcription of the nucleic acid sequence. Such plasmids, as well as other expression vectors, are well known to those of ordinary skill in the art.

Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single-stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acid sequences into an expression vector.

A series of individual nucleic acid sequences can also be combined by utilizing methods that are known to those having ordinary skill in the art (e.g., U.S. Pat. No. 4,683,195). For example, each of the desired nucleic acid sequences can be initially generated in a separate PCR. Thereafter, specific primers are designed such that the ends of the PCR products contain complementary sequences. When the PCR products are mixed, denatured, and reannealed, the strands may have matching sequences at their 3' end overlap and can act as primers for each other. Extension of this overlap by DNA polymerase produces a molecule in which the original sequences are "spliced" together. In this way, a series of individual nucleic acid sequences may be "spliced" together and subsequently transduced into a host cell simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli* (see Shine et al. (1975), *Nature* 254:34 and Steitz, *Biological Regulation and Development: Gene Expression* (ed. R. F. Goldberger), vol. 1, p. 349, 1979, Plenum Publishing, NY).

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter (see deBoer et al. (1983) *Proc Natl Acad Sci USA*, 80:21-25). As will be appreciated by those of ordinary skill in the art, these and other expression vectors may be used in the present invention, and the invention is not limited in this respect.

Although any suitable expression vector may be used to incorporate the desired sequences, readily-available expression vectors include, without limitation, plasmids, such as pSC101, pBR322, pBBR1MCS-3, pUR, pEX, pMR100, pCR4, pBAD24, pUC19, and bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

Methods of Producing and Culturing Host Cells of the Invention

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of a current to increase the permeability of cells to nucleic acid sequences) may be used to transfect the host cell. Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the necessary nucleic acid sequences.

Once the host cell has been transformed with the expression vector, the host cell is allowed to grow. Methods of the invention include culturing the host cell such that recombinant nucleic acids in the cell are expressed. For microbial hosts, this process entails culturing the cells in a suitable medium. Typically cells are grown at 35° C. in appropriate media. Preferred growth media in the present invention are common commercially prepared media such as Luria Bertani (LB) broth, Sabouraud Dextrose (SD) broth or yeast medium (YM) broth. Other defined or synthetic growth media may also be used, and the appropriate medium for growth of the particular host cell will be known by someone skilled in the art of microbiology or fermentation science. One or more unique host cells (with different genetic modifications) may be grown together as a co-culture such that more than one type of biomass polymer may be degraded in single culture.

According to some aspects of the invention, the culture media contains a carbon source for the host cell. Such a "carbon source" generally refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, etc. These include, for example, various monosaccharides, such as glucose, xylose, and arabinose, disaccharides, such as sucrose, oligosaccharides, polysaccharides, biomass polymers, such as cellulose and hemicellulose, saturated or unsaturated fatty acids, succinate, lactate, acetate, ethanol, etc., or mixtures thereof. In preferred embodiments of the invention, the carbon source is one or more biomass polymers such as cellulose and hemicellulose. Multiple biomass polymers may be generated by treating plant biomass with ionic liquid. This treated biomass may then be added to a culture so that the culture contains more than one biomass polymer. The carbon source can additionally be a product of photosynthesis, including, but not limited to, glucose.

In addition to an appropriate carbon source, fermentation media must contain suitable minerals, salts, cofactors, buffers and other components, known to those skilled in the art, suitable for the growth of the cultures and promotion of the enzymatic pathways necessary for production of fatty acid-derived molecules. Reactions may be performed under aerobic or anaerobic conditions where aerobic, anoxic, or anaerobic conditions are preferred based on the requirements of the microorganism. As the host cell grows and/or multiplies, the enzymes necessary for producing alcohols and branched-chain hydrocarbons are expressed.

Alcohols and Branched-Chain Hydrocarbons of the Invention

The present invention provides for the production of alcohols and branched-chain hydrocarbons. The alcohols and branched-chain hydrocarbons include, without limitation, butanol and pinene. The alcohols and branched-chain hydrocarbons of the present invention are useful as fuels, as a chemical source of energy that can be used as an alternative to petroleum-derived fuels, ethanol and the like.

Alcohols of the invention include any C4 to C20 alcohol that is linear or branched. The alcohol may be saturated or unsaturated. In preferred embodiments, the alcohol is butanol. Branched-chain hydrocarbons of the invention include cyclic hydrocarbons (e.g., cycloalkanes and cycloalkenes). The branched-chain hydrocarbons may be bicyclic. Further, they may be saturated or unsaturated and may or may not be partially oxidized. In preferred embodiments, the branched-chain hydrocarbon is pinene.

The present invention provides for an isolated alcohol or branched-chain hydrocarbon produced from the method of the present invention. Isolating the alcohol or branched-chain hydrocarbon involves separating at least part or all of the host cells, and parts thereof, from which the alcohol or branched-chain hydrocarbon was produced, from the isolated alcohol or branched-chain hydrocarbon. The isolated alcohol or branched-chain hydrocarbon may be free or essentially free of impurities formed from at least part or all of the host cells, and parts thereof. The isolated alcohol or branched-chain hydrocarbon is essentially free of these impurities when the amount and properties of the impurities remaining do not interfere in the use of the alcohol or branched-chain hydrocarbon as a fuel, such as a fuel in a combustion reaction.

The present invention also provides for a combustible composition comprising an isolated alcohol or branched-chain hydrocarbon and cellular components, wherein the cellular components do not substantially interfere in the combustion of the composition. The cellular components include whole cells or parts thereof. The cellular components are derived from host cells which produced the alcohol or branched-chain hydrocarbon.

The fatty acid-derived compounds of the present invention are also useful in the synthesis of alkanes, alcohols, and esters for various uses as a renewable fuel. In addition, the fatty acid-derived compounds can also be used as precursors in the synthesis of therapeutics, or high-value oils, such as a cocoa butter equivalent.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

The invention having been described, the following examples are offered to illustrate the subject invention by way of illustration, not by way of limitation.

EXAMPLES

Example 1

Expression of Secreted Endocellulases in E. coli

The first step of lignocellulose metabolism is hydrolysis of the cellulose and hemicellulose by secreted cellulase and hemicellulase enzymes, respectively (FIG. 1B). It was previously observed that the Clostridium stercorarium endoxylanase Xyn10B could be produced extracellularly by E. coli when fused with the protein OsmY (Steen et al., Nature 463, 559 (2010)), a fusion shown to enable protein export (Qian et al., Biotechnol Bioeng 101, 587 (2008)). To find a cellulase exportable by E. coli, a library of cellulase catalytic domains was expressed as OsmY fusions (Table 1).

Selection and Optimization of Cellulase Genes

The set of cellulases was chosen to maximize diversity within family 5 endocellulases. First, the CAZy database was used to collate all known family 5 enzymes (Cantarel et al., Nucleic Acids Research 37, D233 (2009)). At the time this work was done, there were 689 such enzymes in the database. The enzymes were aligned using Muscle (Edgar, Nucleic Acids Research 32, 1792 (2004)) and then ten of the enzymes were selected to maximize diversity using HyperTree (Bingham & Sudarsanam, Bioinformatics 16, 660 (2000)). The ten genes were then optimized for expression in E. coli using GeneDesigner and synthesized by DNA 2.0 (Villalobos, et al., Bmc Bioinformatics 7, (2006)).

Table 1 shows the list of tested cellulases.

TABLE 1

| Cellulase Number | Source Organism | Uniprot ID |
| --- | --- | --- |
| 0 | Xylella fastidiosa 9a5c | Q9PF60 |
| 1 | Aspergillus niger IFO 31125 | Q9C3Z7 |
| 2 | Epidinium caudatum | Q9XXV3 |
| 3 | Macrophomina phaseolina | Q12637 |
| 4 | Globodera rostochiensis | O44078 |
| 5 | Cellvibrio mixtus | O07652 |
| 6 | Unknown thermophilic bacterium grown on lignocellulose | Q60054 |
| 7 | Bacillus sp. D04 | Q45430 |
| 8 | Neocallimastix patriciarum | O59943 |
| 9 | Prevotella ruminicola | O06842 |

Cloning of pGB012 Plasmid for Enzyme Export

The osmY gene (native sequence) was amplified from synthetic DNA (DNA 2.0) using the primers GEB030309-OsmY-nolink-BamHI.rev and GEB030309-OsmY-Bgl2.for and digested with the restriction enzymes BglII and XhoI. The digested product was ligated into BglII-XhoI-digested plasmid pBbE5a-RFP, producing the plasmid pGB012. pGB012 was digested with BamHI and XhoI, enabling genes digested with BglII and XhoI to be ligated into pGB012. Protein fusions were generated with OsmY joined to the N-terminus via a glycine-serine linker, as per the BglBrick standard (Anderson et al., J Biol Eng 4, 1 (2010)). The primers and plasmids used for constructing pGB012 are listed in Table 2.

TABLE 2

| Primer/Plasmid Name | Primer Sequence/Plasmid Description | SEQ ID NO: |
| --- | --- | --- |
| GEB030309-OsmY-Bgl2.for | AGCTAAAGATCTagcaggaggaaaaaaaaatgactatgac | 1 |
| GEB030309-OsmY-nolink-BamHI.rev | TCATTACTCGAGTTAGGATCCGCTGCCCTTA GTTTTCAGATCATT | 2 |
| pBbE5a-RFP | $Amp^R$/ColE1/$P_{lacUV5}$-rfp | |
| pGB012 | $Amp^R$/ColE1/$P_{lacUV5}$-osmY | |

Cloning of Cellulase Genes into pGB012 for Cellulase Screening

Cellulase genes (cellulase numbers 0-9 in Table 1) were amplified from the synthetic gene library received from DNA 2.0. The primers are shown in Table 3. PCR fragments were digested with BglII and XhoI and ligated into BamHI/XhoI-digested pGB012.

Table 3 shows a list of primers used to clone cellulases into pGB012.

TABLE 3

| Primer Name | Primer sequence | SEQ ID NO: |
|---|---|---|
| Cel9.F | CTACGGAATTCATGAGATCTATTAACCAAAATGCAACCTA | 3 |
| Cel9.R | GTAGTCCTCGAGTTTGGATCCGTTGTTGTACGCCTCTTGCA | 4 |
| Cel8.F | CTACGGAATTCATGAGATCTATCCGCGATATCTCCTCCAA | 5 |
| Cel8.R | GTAGTCCTCGAGTTTGGATCCTTTCTTTTCTACGGCGTGTA | 6 |
| Cel7.F | CTACGGAATTCATGAGATCTATCCGCAGCCCAGCGTCCGC | 7 |
| Cel7.R | GTAGTCCTCGAGTTTGGATCCGGTGCTGTCCTTAGTACCCA | 8 |
| Cel6.F | CTACGGAATTCATGAGATCTCGTGAGCAAAGCCATTATGA | 9 |
| Cel6.R | GTAGTCCTCGAGTTTGGATCCCAGATAACGAATGATCTGTT | 10 |
| Cel5.F | CTACGGAATTCATGAGATCTTGGAACGCATCTGACGTACC | 11 |
| Cel5.R | GTAGTCCTCGAGTTTGGATCCCTTATTATCTTTCAGCATAA | 12 |
| Cel4.F | CTACGGAATTCATGAGATCTAATGCACTGACCGCAACTCC | 13 |
| Cel4.R | GTAGTCCTCGAGTTTGGATCCAACACCAGTGCTTTTCTTTT | 14 |
| Cel3.F | CTACGGAATTCATGAGATCTACTTCTACTCTGAAAGCCGC | 15 |
| Cel3.R | GTAGTCCTCGAGTTTGGATCCAACCAGCAGCGCGGAACGAC | 16 |
| Cel2.F | CTACGGAATTCATGAGATCTGGTTTCGGCTGGAACCTGGG | 17 |
| Cel2.R | GTAGTCCTCGAGTTTGGATCCCTTCGCCGCGTTGATCAGCG | 18 |
| Cel1.F | CTACGGAATTCATGAGATCTCACGGCCCAGGTCACAAAAA | 19 |
| Cel1.R | GTAGTCCTCGAGTTTGGATCCCAGGTACGCTTCCAGAATGT | 20 |
| Cel0.F | CTACGGAATTCATGAGATCTGTTTTCTCCTATTCTATTTC | 21 |
| Cel0.R | GTAGTCCTCGAGTTTGGATCCGTCCTTGCCGTTCCACAGCT | 22 |

Cloning of Cel into pGB012

Cel was amplified from synthetic DNA (DNA 2.0) using the primers GEB030909-BB-Cel7.for and GEB030909-BB-Cel7.rev (Table 4). PCR products were digested with BglII and XhoI and ligated into pGB012 digested with BamHI and XhoI.

Table 4 shows primers used for cloning cel into pGB012.

TABLE 4

| Primer Name | Primer Sequence | SEQ ID NO: |
|---|---|---|
| GEB030909-BB-Cel7.for | attcatg agatct ATC CGC AGC CCA GCG TC | 23 |
| GEB030909-BB-Cel7.rev | TCATTACTCGAGTTAGGATCCTTAGGTGCT GTCCTTAGTACCCAGGATATT | 24 |

Cellulase Screening

Two cultures each of E. coli strain DH10B cells (Invitrogen, Carlsbad, Calif., USA) cells bearing pGB012 plasmids encoding each individual OsmY-cellulase fusion were grown overnight in LB medium supplemented with 100 µg/mL carbenicillin and inoculated 1/100 into fresh LB. Cultures bearing pGB012 were used as a cellulase-free control. Cultures were grown at 37° C. to an OD at 600 nm of 0.4 and induced by addition of IPTG to 200 µM. Expression proceeded at 37° C. for 20 hours. A sample from each culture was taken, centrifuged to remove the cells, and 200 µL of the supernatant was assayed for endocellulase activity.

Assay for Secreted Endocellulase Activity

Two hundred µL of culture medium was added to 200 µL of 2% azo-carboxymethycellulose (S-ACMCL; Megazyme, Bray, Ireland). Reactions were incubated at 37° C. for 15 minutes before quenching by addition of 1 mL of precipitant solution (0.4 M sodium acetate, 75% ethanol). Quenched reactions were centrifuged at 13,000 rpm for 1 minute to pellet the undigested CMC, and enzyme activity was measured by determining the absorbance (590 nm) of the liberated Remazolbrilliant Blue R dye in the supernatant.

DNS Assay for Secreted Endocellulase Activity

To test activity of Cel on IL-treated switchgrass (see Example 5), 0.1 g (wet weight, 13 mg dry) of IL-treated switchgrass was incubated in 5 mL sterile-filtered LB medium containing secreted OsmY-Cel at 37° C. Soluble sugars released by hydrolysis were detected using the dinitrosalicylic acid (DNS) assay (Miller, *Analytical Chemistry* 31, 426 (1959)). DNS reacts with sugar reducing ends to produce 3-amino, 5-nitrosalicylic acid, which is detected by measuring absorbance at 575 nm.

Results of Endocellulase Activity Assays

Figure 2:
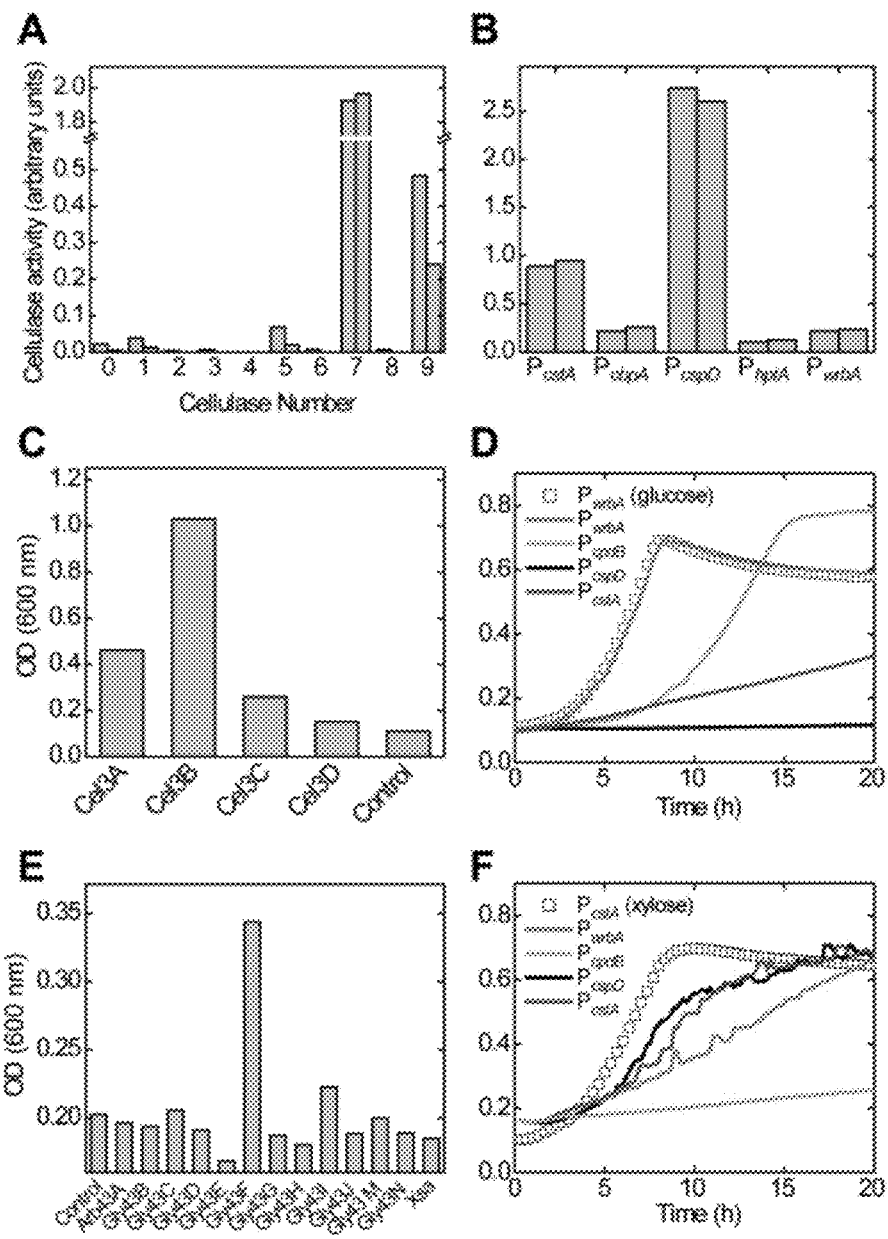
FIG. 2 shows assembling of biological parts required for lignocellulose hydrolysis and consumption by *E. coli*. Part A demonstrates secretion of cellulases. Cellulases were expressed as fusions with the OsmY protein, and extracellular cellulase activity measured using an azo-CMC assay. Cellulase identities that correspond to the numbers used can be found in Table 1. Measurements from biological duplicates have been shown. Part B demonstrates extracellular endocellulase activity levels of cellulase #7 from Table 1 (Cel from *Bacillus* sp. D04) when expressed under the control of several native *E. coli* promoters after 20 hours of growth in LB medium. Measurements from biological duplicates have been shown. Part C demonstrates growth after 18 hours in M9/0.2% cellobiose medium of *E. coli* expressing four β-glucosidases from *Cellvibrio japonicus*. Part D demonstrates growth curves on MOPS-M9/0.5% cellobiose medium when expressing β-glucosidase cel3A under control of *E. coli* promoters. A growth curve on glucose is shown for comparison. Part E demonstrates growth of *E. coli* in MOPS-M9/0.2% xylodextrins after 15 hours, enabled by expression of xylobiosidases. Part F shows growth curves on enzymatically hydrolyzed xylan of *E. coli* expressing the xylobiosidase Gly43F under control of *E. coli* promoters, with a growth curve on xylose for comparison. Each curve was an average of two separate experiments. For growth curves on glucose and xylose, half of the data points have been omitted for clarity.
Figure 3:
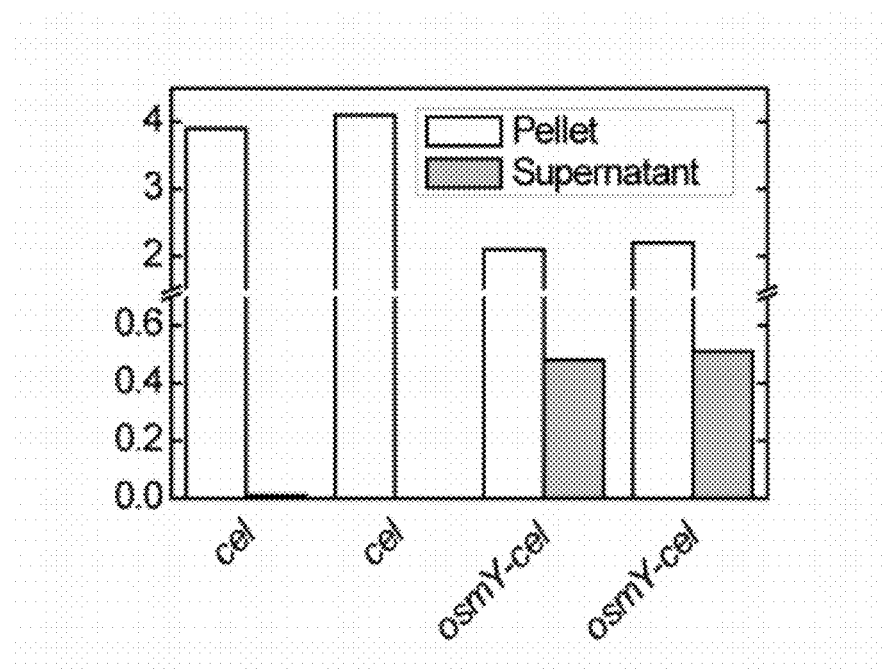
FIG. 3 shows that N-terminal fusions of the *E. coli* protein OsmY with the Cel cellulase increased levels of extracellular cellulase activity relative to Cel alone, likely via protein secretion. *E. coli* MG1655 cells bearing plasmids expressing either osmY-cel or cel under control of the $P_{cspD}$ promoter were grown in LB medium with 100 µg/mL carbenicillin for 24 hours. One mL culture samples were centrifuged and the growth medium removed. The cell pellet was lysed and azo-CMC assays were performed on both the lysate and the culture medium.

The results of the azo-CMC activity assay to measure cellulase activity indicate that expression of two of the 10 OsmY-cellulase fusions generated endocellulase activity in the growth medium (FIGS. 2A, 3).

Additionally, the results of the DNS assay to measure cellulase activity indicate that the Cel protein from *Bacillus* sp.

Figure 4:
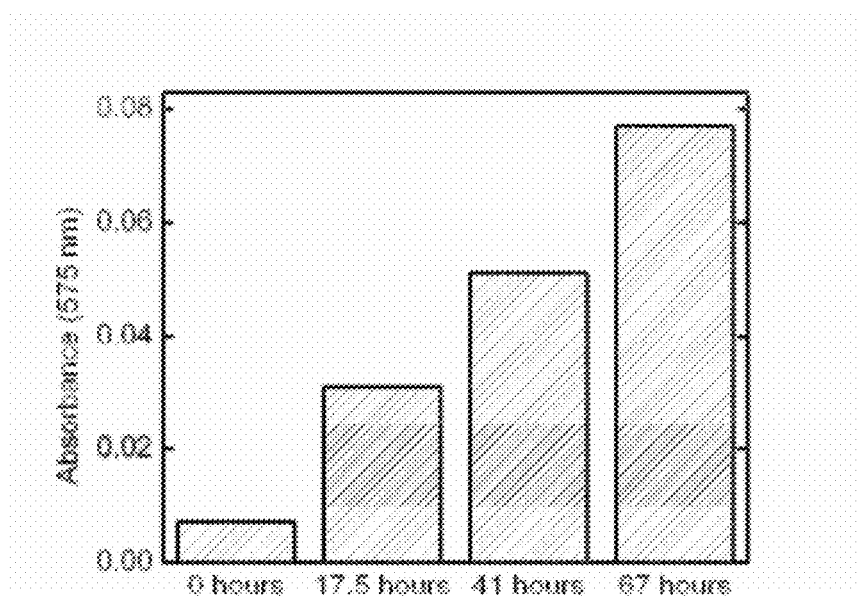
FIG. 4 shows that the endocellulase Cel hydrolysed IL-treated switchgrass.

D04 (cellulase number 7 in Table 1) was able to hydrolyze IL-treated switchgrass (FIG. 4).

Selection of Native *E. coli* Promoters for Enzyme Expression

Native *E. coli* promoters were used to avoid the need for an exogenous chemical inducer to activate biomass consumption and to avoid cross-activation with IPTG-inducible biosynthetic pathways used here. Reasoning that hydrolase expression should occur when the *E. coli* is starved of carbon in order to liberate more sugars from the growth medium, a small selection of promoters that increase in transcriptional activity prior to stationary phase (A. Zaslayer et al., *Nature Methods* 3, 623 (2006)) or that were activated by the gene regulator CRP (Keseler et al., *Nucleic Acids Research* 37, D464 (2009)), were chosen for the study.

Construction of Plasmids for *E. coli* Promoter-Driven Expression

A fragment of pBbA5a-RFP was amplified using primers GEB052209-RK.for and GEB052209-RK.rev (Table 5). Promoters were amplified from *E. coli* MG1655 genomic DNA using the primers shown below in Table 4, and promoters and plasmids were joined using the sequence- and ligation-independent cloning method (SLIC) (Li et al., *Nature Methods* 4, 251 (2007)), replacing the lacI gene and the lacUV5 promoter with the native promoter while retaining the rfp gene downstream. Promoter-RFP plasmids were subsequently digested with BglII-XhoI to remove the rfp gene, and were ligated with BglII-XhoI-digested gene OsmY-Cel7.

Table 5 shows a list of primers and plasmid for construction of plasmids bearing *E. coli*-promoter driven expression.

TABLE 5

| Primer/<br>Plasmid<br>Name | Primer Sequence/Plasmid Description | SEQ<br>ID<br>NO: |
|---|---|---|
| GEB052209-<br>cpdB.for | ctaatgagtgagctaacttacattaattg TTTCTCCACCTCGTCTCTGTG | 25 |
| GEB052209-<br>cpdB.rev | tatctccttcttaaaagatcttttgaattcCAGGGACATCCTTTTATCATCGG | 26 |
| GEB052209-<br>ompA.for | Ctaatgagtgagctaacttacattaattg<br>AGTAAATTTAGGATTAATCCTGGAACTTT | 27 |
| GEB052209-<br>ompA.rev | tatctccttcttaaaagatcttttgaattc TTTTTGCGCCTCGTTATCATC | 28 |
| GEB052209-<br>cstA.for | ctaatgagtgagctaacttacattaattg<br>AACCCGACAGAATTAGATGAGA | 29 |
| GEB052209-<br>cstA.rev | tatctccttcttaaaagatcttttgaattc AGTTGTTATCCGTGTGCGT | 30 |
| GEB052209-<br>hptA.for | Ctaatgagtgagctaacttacattaattg<br>CACCATTTCAATTCATTAATATTTTAGTAGC | 31 |
| GEB052209-<br>hptA.rev | tatctccttcttaaaagatcttttgaattc<br>ATCTCTAACCATATGATTTAAAAACAAATC | 32 |
| GEB052209-<br>wrbA.for | ctaatgagtgagctaacttacattaattg<br>TCTCCAATAATTATCCATAAGCCG | 33 |
| GEB052209-<br>wrbA.rev | tatctccttcttaaaagatcttttgaattc TTCTAACCACTCCTCGTGTTA | 34 |
| GEB052209-<br>cspD.for | ctaatgagtgagctaacttacattaattg<br>TTGTCAGTTATCATCTTCGGTTACG | 35 |
| GEB052209-<br>cspD.rev | tatctccttcttaaaagatcttttgaattc GCTTCGACATCCTTCGCAA | 36 |
| GEB052209-<br>cbpA.for | ctaatgagtgagctaacttacattaattg<br>GCGTCTATAAAATTTAATAAATAATGACGC | 37 |
| GEB052209-<br>cbpA.rev | tatctccttcttaaaagatcttttgaattc<br>AGCGTTATCTCGCGTAAATCAAC | 38 |
| GEB052209-<br>RK.for | GAATTCAAAAGATCTTTTAAGAAGGAGATATACA | 39 |
| GEB052209-<br>RK.rev | CAATTAATGTAAGTTAGCTCACTCATTAGG | 40 |
| pBbA5a-RFP | Amp$^R$/p15A/P$_{lacUV5}$-rfp | |

Measurement of Native Promoter-Driven Cellulase Activity

Plasmids bearing osmY-cel under control of several *E. coli* promoters were introduced into MG1655 cells, and transformants were grown in LB medium with 100 ng/mL carbenicillin for 20 hours before endocellulase activity present in the supernatant was measured as described above.

Results: Promoter-Driven Cellulase

Expression of osmY-cel was placed under the control of several *E. coli* promoters. The promoter for the cspD gene ($P_{cspD}$) to drive expression of osmY-cel resulted in the highest cellulase activity (FIG. 2B).

Example 2

Expression of β-Glucosidases in *E. coli*

The soluble oligosaccharides that are produced by enzymatic hydrolysis of cellulose, such as cellobiose, cannot be metabolized by *E. coli* MG1655. To further hydrolyze the cellobiose products into glucose, four β-glucosidases cloned from *Cellvibrio japonicus*, a Gram-negative cellulolytic bacterium, were screened and tested to determine if their expression in *E. coli* could permit growth on cellobiose (FIG. 1B) (Rixon et al., *Biochemical Journal* 285, 947 (1992); Deboy et al., *Journal of Bacteriology* 190, 5455 (2008)).

Cloning of β-Glucosidases from *Cellvibrio japonicus*

β-glucosidase genes were amplified from the genomic DNA of *C. japonicus* NCIMB 10462 using primers listed in Table 6, and the PCR products were digested using BglII and XhoI and ligated into BglII-XhoI-digested plasmid pBbE5a-RFP (Table 2).

Table 6 shows a list of primers used for cloning β-glucosidase genes from *C. japonicus*.

TABLE 6

| Primer Name | Primer Sequence | SEQ ID NO: |
|---|---|---|
| GEB031209-CJ-cel3A.for | AGCTAA AGATCT aggaggaa aaa aatgaaagatgatttccctcaacgc | 41 |
| GEB031209-CJ-cel3A.rev | TCA TTA CTC GAG TTA GGA TCC TTA ggggcaggcgacgtc | 42 |
| GEB031209-CJ-cel3B.for | AGCTAA AGATCT aggaggaa aaa aatgctgtggccaaaagtcacc | 43 |
| GEB031209-CJ-cel3B.rev | TCATTACTCGAGTTAGGATCCTTA accaacaacaccaaatgttccatg | 44 |
| GEB031209-CJ-cel3C.for | AGCTAA AGATCT aggaggaa aaa a atgcacttgtcctgcaaaacc | 45 |
| GEB031209-CJ-cel3C.rev | TCA TTA CTC GAG TTA GGA TCC TTActcgggacacgtaatcgtctg | 46 |
| GEB031209-CJ-cel3D.for | AGCTAA AGATCT aggaggaa aaa a atgaaaaaacgacatccactggc | 47 |
| GEB031209-CJ-cel3D.rev | TCA TTA CTC GAGTTAGGATCCTTA tttcatgagggattggatgtcctg | 48 |

β-Glucosidase Screening

BL21 cells bearing β-glucosidase genes (plasmid backbone pBbE5a) were grown overnight in LB medium with 100 μg/mL carbenicillin, transferred 1/100 into M9/0.2% cellobiose medium with 100 μg/mL carbenicillin, and allowed to grow for 18 hours at 37° C. before OD measurements were taken. M9 medium was prepared using M9 salts (Sigma, St. Louis, Mo., USA) with the addition of 2 mM $MgSO_4$ and 0.1 mM $CaCl_2$, plus antibiotics as described below. A cell line bearing a plasmid with a β-xylosidase (pBbE5a-gly43E) was used as a control.

Results: β-Glucosidase Screening

As shown in FIG. 2C, *E. coli* grew best on cellobiose when expressing either cel3A or cel3B.

Native Promoter Selection

For Cel3B-native promoter screening, plasmids bearing cel3B under control of several *E. coli* promoters were introduced into BL21 cells, and transformants were grown in LB medium with 100 μg/mL carbenicillin overnight and inoculated 1/25 into a 96-well plate with 200 μL of M9/0.2% cellobiose medium or M9/0.2% glucose medium with 200 μg/mL carbenicillin. Growth was monitored with a microplate incubator and reader (Tecan Systems, Inc., San Jose, Calif., USA).

For Cel3A-native promoter screening, plasmids bearing cel3A under control of one of several promoters were introduced into MG1655 cells, and overnight cultures were inoculated 1/40 into 800 μL of MOPS-M9/0.5% cellobiose or MOPS-M9/0.5% dextrose with 100 μg/mL carbenicillin in a 24-well plate. MOPS-M9 medium (Teknova, Hollister, Calif., USA) was prepared as per the manufacturer's instructions, except the carbon source (glucose) was replaced by other sugars as described. Growth was monitored with a microplate incubator and reader (Tecan Systems, Inc.).

Results: Promoter-Driven β-Glucosidase

Figure 5:
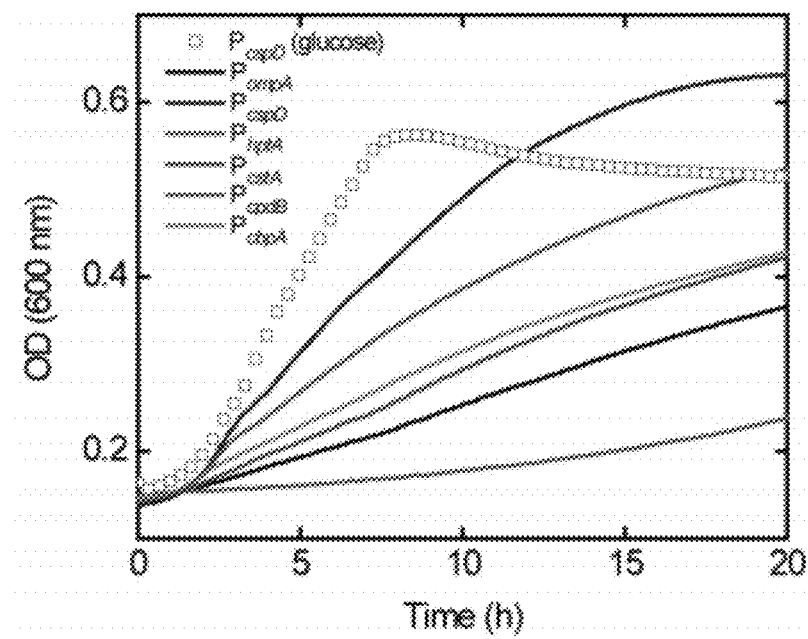
FIG. 5 shows growth curves on cellobiose by *E. coli* expressing *C. japonicus* beta-glucosidase cel3B under control of *E. coli* promoters. Cells were inoculated 1/25 from cultures grown overnight in LB medium with 100 µg/mL carbenicillin into 100 µL M9/0.2% cellobiose medium with 200 µg/mL carbenicillin A growth curve on M9/0.2% glucose medium with 200 µg/mL carbenicillin has been shown for comparison. Growth was monitored using a 96-well plate at 37° C. in a microplate reader (Tecan Systems Inc., San Jose, Calif., USA). Only half of the data points in the glucose curve have been shown for clarity.

The genes cel3A and cel3B were expressed using several native *E. coli* promoters to determine which promoter-enzyme combination permitted the fastest growth on cellobiose. A strain expressing cel3A under the control of the wrbA promoter ($P_{wrbA}$) grew on cellobiose as fast as on glucose (FIGS. 2D, 5).

Example 3

Expression of Xylobiosidases in *E. coli*

To enable growth of *E. coli* on xylodextrins, the oligosaccharide products of xylan hydrolysis, 12 xylobiosidase genes from the genome of *C. japonicus* (Deboy et al., *Journal of Bacteriology* 190, 5455 (2008)) and xsa from *Bacteroides ovatus*, which can enable growth on xylan when expressed with xyn10B, were screened (Steen et al., *Nature* 463, 559 (2010)).

Cloning of xyn10B into pGB012

The gene xyn10B was amplified from synthetic DNA (DNA 2.0) using the primers GEB030909-BB-XynB.for and GEB030909-BB-XynB.rev (Table 7). PCR products were digested with BglII and XhoI and ligated into pGB012 digested with BamHI and XhoI.

Table 7 shows a list of primers for cloning xyn10B into pGB012.

TABLE 7

| Primer Name | Primer Sequence | SEQ ID NO: |
|---|---|---|
| GEB030909-BB-XynB.for | attcatg agatct ATG ACC GGT AAG AAA GCA TTC AAC G | 49 |
| GEB030909-BB-XynB.rev | TCA TTA CTC GAG TTA GGA TCC TTA TTC ACG CAG ACG GGA TGG GTC | 50 |

Cloning of xylobiosidases from *Cellvibrio japonicus* and xsa from *Bacteroides ovatus*

The xylobiosidase genes were amplified from the genomic DNA of *C. japonicus* NCIMB 10462 using primers listed in Table 7, and the PCR products digested using BglII and XhoI and ligated into the plasmid pP$_{cpD}$-rfp/p15A (Table 8) digested with BglII-XhoI. The gene xsa was cloned from pGB-1 (Steen et al., *Nature* 463, 559 (2010)).

Table 8 shows a list of the primers and plasmid used for cloning xylobiosidase genes from *C. japonicus*.

TABLE 8

| Primer/Plasmid Name | Primer Sequence/Plasmid Description | SEQ ID NO: |
|---|---|---|
| GEB030609-arb43A_1.for | taatcc AGATCT aggaggaaaaaaaa atgcccacccaccacc | 51 |
| GEB030609-arb43A_1041.rev | atacca CTCGAG ttt GGATCC TTA tttcaaacgttggctgatgtaactatc | 52 |
| GEB030609-gly43B_1.for | taatcc AGATCT aggaggaaaaaaaa atgcgtccactaaccatccg | 53 |
| GEB030609-gly43B_1695.rev | atacca CTCGAG ttt GGATCC TTA cggcagcgccctataca | 54 |
| GEB030310-Gly43C1.for | taatcc AGATCT aggaggaaaaaaaa atgtataagcgtattttggccggta | 55 |
| GEB030310-Gly43Cend.rev | atacca CTCGAG TTA GGATCC TTA ctatttcaagcgtgtcagcgtc | 56 |
| GEB030609-gly43D_1.for | taatcc AGATCTaggaggaaaaaaaa atgaaaaaatacctatggctttgcttgc | 57 |
| GEB030609-gly43D_1143.rev | atacca CTCGAG ttt GGATCC TTA caccaggcattgtccatcgg | 58 |
| GEB030609-gly43E_1.for | taatcc AGATCT aggaggaaaaaaaa atgaaattgacaagcctggcg | 59 |
| GEB030609-gly43E_1275.rev | atacca CTCGAG ttt GGATCC TTA ttcattgacatcaacaacattttgccc | 60 |
| GEB030310-Gly43F1.for | taatccAGATCTaggaggaaaaaaaaatgtctacagaaaatga agttgttgattacaa | 61 |
| GEB030310-Gly43Fend.rev | atacca CTCGAGTTAGGATCCTTA ctaatcacgatagggatgaatcgttttaatt | 62 |
| GEB030609-gly43E_1.for | taatcc AGATCT aggaggaaaaaaaa atgaaattgacaagcctggcg | 63 |
| GEB030609-gly43E_1275.rev | atacca CTCGAG ttt GGATCC TTA ttcattgacatcaacaacattttgccc | 64 |
| GEB030609-gly43G_1.for | taatcc AGATCT aggaggaaaaaaaa atgccattaccactgcgacat | 65 |
| GEB030609-gly43G_1113.rev | atacca CTCGAG ttt GGATCC TTA aactatgggttggatactgccatc | 66 |
| GEB030609-gly43H_1.for | taatcc AGATCT aggaggaaaaaaaa atgttagatgcaacccgtaggg | 67 |
| GEB030609-gly43H_1653.rev | atacca CTCGAG ttt GGATCC TTA cgttgacgagcgcgcc | 68 |
| GEB030609-gly43I_1.for | taatcc AGATCT aggaggaaaaaaaa atgttcaaacctgtttctatccgacg | 69 |
| GEB030609-gly43I_1659.rev | atacca CTCGAG ttt GGATCC TTA cttaaccaacggcgtcacct | 70 |
| GEB030310-Gly43J1.for | taatcc AGATCT aggaggaaaaaaaa atgccgctaaaaacgctagcc | 71 |
| GEB030310-Gly43Jend.rev | atacca CTCGAG TTA GGATCC TTA gggtgactgcctgacatgc | 72 |
| GEB030609-gly43L_1.for | taatcc AGATCT aggaggaaaaaaaa atgccaaacctgatcaacccg | 73 |

TABLE 8-continued

| Primer/Plasmid Name | Primer Sequence/Plasmid Description | SEQ ID NO: |
|---|---|---|
| GEB030609-gly43L_1071.rev | atacca CTCGAG ttt GGATCC TTA ttttgtactctgtttgtgtgtcactaag | 74 |
| GEB030609-gly43M_1.for | taatcc AGATCT aggaggaaaaaaaa atggacgctgtctttttttcgg | 75 |
| GEB030609-gly43M_1041.rev | ataccaCTCGAG ttt GGATCC TTA cgcaccgcgcacca | 76 |
| GEB030609-gly43N_1.for | taatcc AGATCT aggaggaaaaaaaa atgacaacctccctgaattcc | 77 |
| GEB030609-gly43N_1002.rev | atacca CTCGAG ttt GGATCC TTA cttggcggctttttaacccg | 78 |
| GEB030909-BB-Xsa.for | attcatg agatct ATG AAA ACT GAA AAA CGT TAC CTG GTT CC | 79 |
| GEB030909-BB-Xsa.rev | TCATTACTCGAGTTAGGATCCTTATTCATC TTTACCTTCGATAGTGATGATAC | 80 |
| $P_{cspD}$-rfp/p15A | $Amp^R$/p15A/$P_{cspD}$-rfp | |

β-Xylosidase Screening

E. coli DH10B cells carrying β-xylosidase genes under control of $P_{cspD}$ were grown overnight in LB medium with 100 µg/mL carbenicillin The cultures did not grow at similar rates, likely due to the over-expression of proteins that may be toxic to E. coli. Cultures were inoculated into MOPS-M9/0.2% xylan with 0.5 µg/mL thiamin and 100 µg/mL carbenicillin, into which sterile LB containing secreted OsmY-Xyn10B had been added (1/10 volume) to hydrolyze the xylan into xylodextrins. Growth was monitored on a 96 well plate with a microplate reader (Tecan Systems Inc.).

Results: β-Xylosidase Screening

Expression of gly43F enabled growth on enzymatically hydrolyzed xylan (FIG. 2E).

DNS Assay for Endoxylanase Activity

To test activity of Xyn10B on IL-treated switchgrass (see Example 5), 0.2 g (wet weight) of IL-treated switchgrass was incubated with 5 mL sterile-filtered LB medium containing OsmY-Xyn10B at 37° C. Released sugars were detected using the DNS assay as described in Example 1.

Results of Endoxylanase Activity Assays

Figure 6:
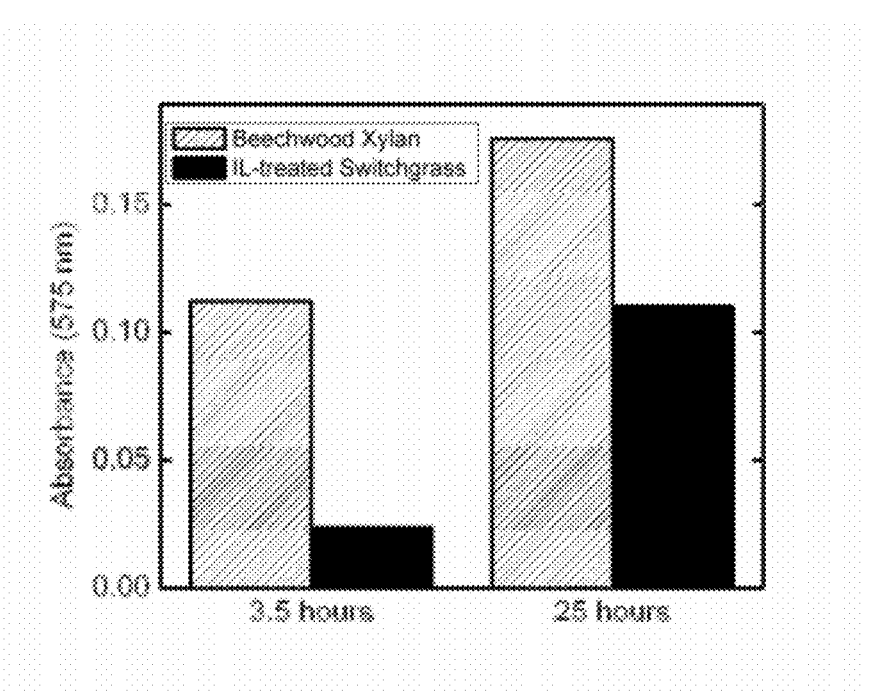
FIG. 6 shows that endoxylanase Xyn10B released soluble sugars from IL-treated switchgrass. Sugars released from beechwood xylan by OsmY-Xyn10B have been shown for comparison.

As shown in FIG. 6, the endoxylanase Xyn10B was able to release soluble sugars from IL-treated switchgrass. Sugars released from 5 mg of beechwood xylan by OsmY-Xyn10B are also shown.

Native Promoter Selection

For gly43F-native promoter screening, plasmids carrying gly43F under control of several E. coli promoters were introduced into MG1655 cells. Cells were grown overnight in LB medium with 100 µg/mL carbenicillin and inoculated 1/40 into 800 µL of MOPS-M9/0.5% beechwood xylan or xylose with 100 µg/mL carbenicillin supplemented with 5% of sterile LB containing secreted OsmY-Xyn10B on a 24-well plate. Growth was monitored with a microplate reader (Tecan Systems Inc.).

Results: Promoter-driven Endoxylanase

Expression of gly43F under the control of native E. coli promoters was tested to optimize growth on xylodextrins. Results showed that expression of gly43F using the promoters $P_{cstA}$ or $P_{cspD}$ enabled a growth rate on xylodextrins that compared well with growth in xylose (FIG. 2F).

Example 4

Growth of Engineered E. coli on Model Substrates

Figure 7:
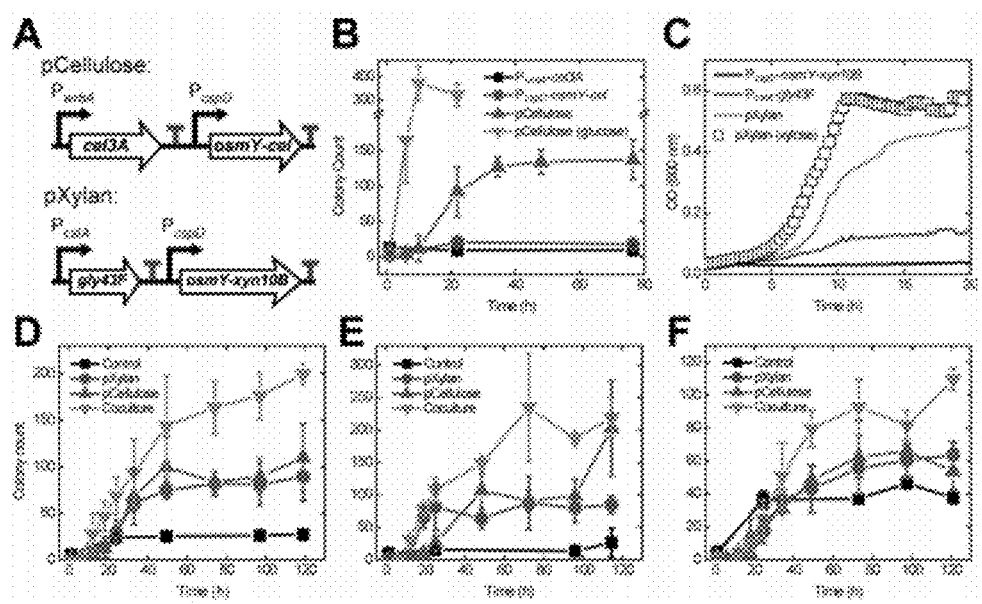
FIG. 7 shows that the engineered *E. coli* grew on model cellulosic substrates and IL-treated plant biomass. Part A shows the gene schematics for the pCellulose and pXylan plasmids, designed to enable *E. coli* to metabolize cellulose and xylan, respectively. Part B shows growth on phosphoric acid swollen cellulose (PASC) monitored by serial dilution, plating, and colony counting. Cells expressing either Cel3A or OsmY-Cel alone, or containing the pCellulose plasmid, were grown in MOPS-M9/0.7% PASC. Growth of the pCellulose-bearing strain in MOPS-M9/0.4% glucose has been shown for comparison. Each colony represented $10^7$ cells/mL in the original growth medium. Part C shows growth of strains expressing either Gly43F or OsmY-XynB alone, or bearing pXylan in MOPS-M9/0.5% beechwood xylan. Growth of pXylan-bearing strain in 0.5% xylose has been shown for comparison. Each curve was an average of three separate growth experiments. Parts D, E, and F show growth on the cellulose and hemicellulose fractions of IL-treated switchgrass, eucalyptus, and yard waste, respectively. Error bars represent standard deviation of biological triplicates, except for the yard waste control strains (biological duplicates).

The two constructs $P_{cspD}$-osmY-cel and $P_{wrbA}$-cel3A were combined into a single plasmid designated pCellulose (FIG. 7A) to enable growth on cellulose. Similarly, the constructs $P_{cspD}$-osmY-xyn10B and $P_{cstA}$-gly43F were combined into a single plasmid, designated pXylan (FIG. 7A).

Construction of pCellulose Plasmid $P_{cspD}$-rfp was introduced onto plasmid pBbS5a by amplifying $P_{cspD}$-rfp using the primers GEB090909-SlicAmpR.for and GEB072709-SLIC-XhoI-term.rev, and the pBbS5a backbone using GEB090909-SlicAmpR.rev and GEB072709-SLIC-XhoI-term.for, and joining the fragments together using SLIC. $P_{cspD}$-osmY-cel with a somewhat weaker ribosome binding site was constructed by amplifying osmY-cel with primers GEB042610-OsmYRBS3.F and GEB030909-BB-Cel7.rev, digested with BglII/XhoI, and ligated into BglII/XhoI-digested plasmid p$P_{cspD}$-rfp/SC101, making plasmid p($P_{cspD}$-RBS3-osmY-cel/SC101). $P_{cspD}$-RBS3-osmY-cel was amplified with the SC101** on and part of the bla gene using the primers GEB032910-T3-CspDp.F and GEB090909-SlicAmpR.rev. The triple terminator was amplified from plasmid pNS2σVL using the primers GEB032910-T3-CspDp.R and GEB032910-Cel3A-T3.F. $P_{wrbA}$-cel3A was amplified from the plasmid p$P_{wrbA}$-cel3A/p15A using the primers GEB032910-Cel3A-T3.F and GEB090909-SlicAmpR.rev, and joined together with the triple terminator fragment using PCR SOEing (Horton et al., Gene 77, 61 (1989)). The fragment $P_{wrbA}$-cel3A-triple terminator was joined with $P_{cspD}$-RBS3-osmY-cel via SLIC. Details about the primers and plasmids are shown in Table 9.

Construction of pXylan Plasmid $P_{cspD}$-osmY-xyn10B was transferred to plasmid pBbS5a by amplifying $P_{cspD}$-osmY-xyn10B from plasmid p$P_{cspD}$-osmY-xyn10B/p15A with the primers GEB090909-SlicAmpR.for and GEB072709-SLIC-XhoI-term.rev, and pBbS5a amplified using GEB090909-SlicAmpR.rev and GEB072709-SLIC-XhoI-term.for. The two fragments were joined using SLIC, and a fragment bearing $P_{cspD}$-osmY-xyn10B with the SC101** on and part of the bla antibiotic resistance marker was amplified using primers GEB032910-T3-CspDp.F and GEB090909-SlicAmpR.rev. A terminator ("triple terminator") was amplified from plasmid pNS2σVL (Dunlop et al., *Nature Genetics* 40, 1493 (2008)) using the primers GEB032910-T3-CspDp.R and GEB032910-Gly43F-T3.F. P$_{cstA}$-gly43F was amplified from the plasmid pP$_{cstA}$-gly43F/p15A using the primers GEB032910-Gly43F-T3.R and GEB090909-SlicAmpR.for. These three fragments were joined together using one-step isothermal in vitro recombination (Gibson et al., *Nature Methods* 6, 343 (2009)). Details about the primers and plasmids are shown in Table 9.

Table 9 shows a list of primers and plasmids for construction of pCellulose and pXylan.

overnight. One hundred mL of sterile cold H$_2$O was added to the solution, causing the cellulose to precipitate. The cellulose was centrifuged and washed repeatedly with cold sterile H$_2$O, and 2.5 mL of 2 M sodium carbonate was added. The cellulose was washed again repeatedly until the pH of the solution was measured to be ~7.

For growth on PASC, triplicates of *E. coli* MG1655 bearing plasmids pCellulose, pP$_{wrbA}$-cel3A/p15A, or P(P$_{cspD}$-RBS3-osmY-cel/SC101**) were grown overnight in LB with 100 μg/mL carbenicillin. Because of the presence of insoluble PASC, spectrophotometric measurements of growth were made by serially diluting a sample 10$^{-6}$ (2 μL in 200 μL three times) in sterile phosphate-buffered saline, and 100 μL of the

TABLE 9

| Primer/Plasmid Name | Primer Sequence/Plasmid Description | SEQ ID NO: |
|---|---|---|
| GEB090909-SlicAmpR.for | ATC ACT CAT GGT TAT GGC AGC ACT GCA TAATTCTCTTAC | 81 |
| GEB090909-SlicAmpR.rev | GTA AGA GAA TTA TGC AGT GCT GCCATAACCATG AGT GAT | 82 |
| GEB032910-Gly43F-T3.R | GTTTGCCGGATCGTCGACCATACTTACT AATCACGATAGGGATGAATCGTTTTAATT | 83 |
| GEB032910-Gly43F-T3.F | AATTAAAACGATTCATCCCTATCGTGAT TAGTAAGTATGGTCGACGATCCGGCAAAC | 84 |
| GEB032910-T3-CspDp.R | GATAACCGTAACCGAAGATGATAACTG ACAAGGGCAGAAAGTCAAAAGCCTCCG | 85 |
| GEB032910-T3-CspDp.F | CGGAGGCTTTTGACTTTCTGCCCTTGTC AGTTATCATCTTCGGTTACGGTTATC | 86 |
| GEB042610-OsmYRBS3.F | AGCTAA AGATCT agcaAgaggaaaaaaaaatgactatgac | 87 |
| GEB072709-SLIC-XhoI-term.for | CTC GAG TAA GGA TCT CCA GGC AT | 88 |
| GEB072709-SLIC-XhoI-term.rev | ATG CCT GGA GAT CCT TAC TCG AG | 89 |
| GEB032910-Cel3A-T3.R | GTTTGCCGGATCGTCGACCATACTTATT AGGGGCAGGCGACGTCTTTTC | 90 |
| GEB032910-Cel3A-T3.F | GAAAAGACGTCGCCTGCCCCTAATAAG TATGGTCGACGATCCGGCAAAC | 91 |
| pP$_{cspD}$-osmY-xyn10B/p15A | Amp$^R$/p15A/P$_{cspD}$-osmY-xyn10B | |
| pBbS5a | Amp$^R$/SC101**/P$_{lacUV5}$-rfP | |
| pP$_{cspD}$-osmY-xyn10B/SC101** | Amp$^R$/SC101**/P$_{cspD}$-osmY-xyn10B | |
| pP$_{cstA}$-gly43F/p15A | Amp$^R$/p15A/P$_{cstA}$-gly43F/p15A | |
| pP$_{cspD}$-rfp/SC101** | Amp$^R$/SC101**/P$_{cspD}$ -rfP | |
| p(P$_{cspD}$-RBS3-osmY-cel/SC101**) | Amp$^R$/SC101**/P$_{cspD}$-RBS3-osmY-cel | |
| pP$_{wrbA}$-cel3A/p15A | Amp$^R$/p15A/P$_{wrbA}$-cel3A | |

Growth on PASC

PASC was prepared largely as described (Zhang et al., *Biomacromolecules* 7, 644 (2006)), with some modifications. One gram of autoclaved Avicel PH-101 (Fluka, St. Louis, Mo., USA) was suspended in 3 mL of sterile deionized H$_2$O, dissolved in 50 mL phosphoric acid (87%) and stirred at 4° C.

10$^{-6}$ dilution was spread on an LB-agar plate. Colonies were counted the next day. All growth curves were performed with biological triplicates (three different colonies).

Growth on Beechwood Xylan

Biological triplicates of *E. coli* MG1655 cells carrying either pXylan, pP$_{cstA}$-gly43F/p15A, or pP$_{cspD}$-osmYxyn10B/SC101** were inoculated into LB with 100 μg/mL carbenicillin and grown at 37° C. for 16 hours. Overnight cultures were inoculated 1/20 into 800 μL MOPS-M9/0.5% xylan or 0.5% xylose medium with 100 μg/mL carbenicillin and grown with shaking in a microplate reader (Tecan Systems Inc.) at 37° C. Curves shown are averages of the triplicates and median-averaged over a 5-point window.

Results of Growth on Model Cellulosic Substrates

Figure 8:
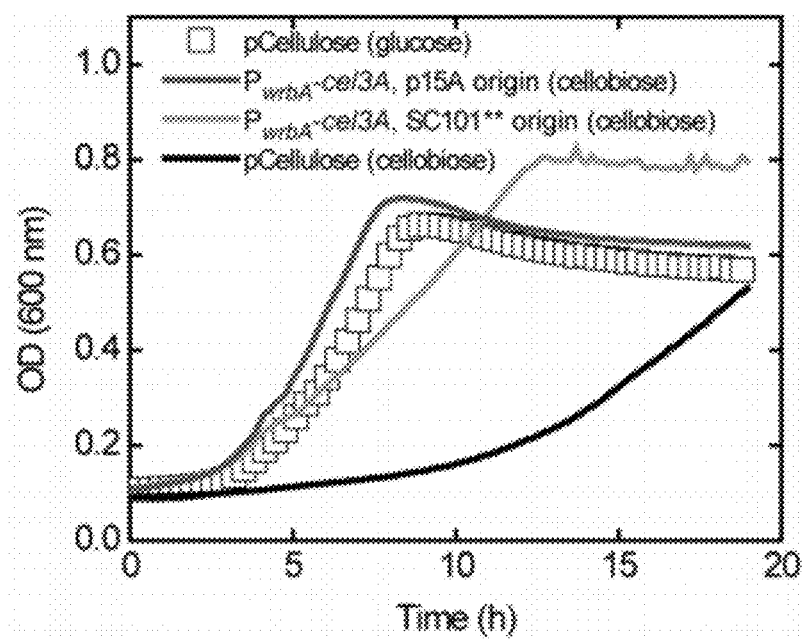
FIG. 8 shows growth curves of *E. coli* MG1655 cells bearing plasmids with $P_{wrbA}$-cel3A only (with p15A or SC101** origin of replication) or pCellulose inoculated 1/40 from overnight cultures in LB medium into MOPS-M9/0.5% glucose or cellobiose. Comparison of the growth curves of the strains bearing plasmids with $P_{wrbA}$-cel3A only suggested that the reduced growth rate of pCellulose on cellobiose was partially due to the lower copy number of the pCellulose plasmid. Each curve was an average of three biological replicates. Only half of the data points in the glucose curve have been shown for clarity.

E. coli bearing pCellulose grew on phosphoric acid swollen cellulose (PASC) as a sole carbon source (FIG. 7B), though growth on cellobiose was slow relative to plasmids bearing $P_{wrbA}$-cel3A alone (FIG. 8). E. coli bearing pXylan grew on beechwood xylan nearly as rapidly as on xylose (FIG. 7C).

Example 5

Growth of Engineered E. coli on Unrefined Plant Biomass

Figure 9:
FIG. 9 shows plant compost gathered from a residential backyard in Berkeley, Calif., USA, before milling and IL pretreatment.

E. coli bearing either pXylan or pCellulose was grown on plant biomass (switchgrass, eucalyptus, and yard waste) treated with the ionic liquid 1-ethyl-3-methyl imidazolium acetate. In particular, use of the IL-treated yard waste (FIG. 9) as feedstock can avoid the costs of growing dedicated energy crops while decreasing landfill usage (Bingham & Sudarsanam, *Bioinformatics* 16, 660 (2000)).

[C$_2$mim][OAc] Ionic Liquid Pretreatment of Biomass

1-Ethyl-3-methylimidazolium acetate ([C$_2$mim][OAx], BASF, purity ≥90%) was used as the ionic liquid. *Eucalyptus globulus* was supplied by Arborgen (Summerville, S.C., USA). Yard waste (FIG. 9) was gathered from a residential back yard in Berkeley, Calif. USA. Biomass was milled and sieved to a particle size of 250-400 μm. Moisture was removed by drying to constant weight in a convection oven at 40° C. A 5% loading of biomass to ionic liquid was used (10 g biomass to 190 g [C$_2$mim][OAc]). The biomass and IL were placed in a 450 mL borosilicate vessel which was placed in a Parr Instrument Company Mini Bench Top Reactor (Part no. 4562). The reactor was purged of air using N$_2$ and the reactants stirred at 300 rpm and heated to 120° C. with venting. The reactor was sealed and the reaction allowed to proceed for 3 hours. Temperature ramp and cooling (to 30° C.) times were approximately 15 and 30 minutes, respectively. Three parts H$_2$O to one part reactant was then added to the cooled reactant whilst stirring vigorously, causing precipitation of the biomass. The precipitated components were filtered for subsequent processing.

Biomass Preparation

Biomass (10-35 grams) precipitated from ionic liquid pretreatment was centrifuged and re-suspended at least six times with 200 mL deionized H$_2$O to remove toxic ionic liquid and collected over Miracloth (Calbiochem, Gibbstown, N.J., USA). Excess water was squeezed from the biomass, and the biomass was added to culture tubes. Some wet biomass was placed into pre-weighed Eppendorf tubes, weighed, lyophilized for at least 2 days, and re-weighed to determine the amount of dry biomass solids. Water was added to the biomass in the culture tubes, and the tubes were sterilized in an autoclave for 20-40 minutes in a liquid cycle. After cooling, MOPS-M9 salts, other nutrients, and antibiotics were added to the biomass.

Growth Curves on Biomass

For biomass medium, 10 mL of MOPS-M9 with biomass and 100 ng/mL carbenicillin were prepared as described above. For growth on plant biomass, *E. coli* MG1655 bearing either plasmid pXylan, pCellulose, or a control plasmid pRK-3 were grown for 18 hours at 37° C. in LB medium containing 100 μg/mL carbenicillin For growth of monocultures on biomass, the biomass medium was inoculated 1/20 (0.5 mL) with either the control plasmid pBbS7a (SC101** ori, ampicillin resistance marker, RFP gene expressed under control of a T7 promoter), pXylan, or pCellulose cultures. For growth of pXylan/pCellulose co-cultures, the biomass medium was inoculated with 0.25 mL pXylan and pCellulose cultures. All growth curves were performed with biological triplicates (three different colonies) with the exception of the yard waste control culture, which was performed in duplicate.

Because of the presence of insoluble plant biomass, spectrophotometric measurements of growth in these were made by serially diluting a sample $10^{-6}$ (2 μL in 200 μL three times) in sterile phosphate-buffered saline, and 100 μL of the $10^{-6}$ dilution was spread on an LB-agar plate. Colonies were counted the next day.

Biomass Washing and Analysis

After the last sample point was collected for serial dilution and plating, the biomass was collected over a 20 μm nylon filter (Millipore, Billerica, Mass., USA) and washed repeatedly with water to remove the *E. coli*. The biomass was lyophilized and weighed to determine the fraction of solids remaining. The percent of biomass that was not solubilized by the enzymes was taken to be the mass of the biomass present in the co-cultures divided by the mass of the biomass present in the control cultures.

Results: Growth on IL-treated Biomass

Both strains grew well on IL-switchgrass, indicating that both the cellulose and hemicellulose components of the switchgrass could be used as carbon sources (FIG. 7D). When the strains were combined and grown on switchgrass as a co-culture, the cells grew to a cell density approximately equal to the sum of the individual monocultures (FIG. 7D), demonstrating growth on both fractions of switchgrass. To obtain an upper estimate of the extent of biomass solubilization by the co-culture, the remaining insoluble biomass was collected on a 20 μm filter to remove the *E. coli* cells. Cel and Xyn10B enzymes reduced the insoluble biomass collected by 22±1%.

Both pXylan and pCellulose monocultures and a co-culture of the two strains grew well in minimal medium containing 4.0% w/v IL-treated eucalyptus (FIG. 7E), the co-culture solubilizing up to 15±1% of the plant biomass.

Similar to the results discussed above, both monocultures and the co-culture grew in minimal medium containing 2.6% w/v yard waste (FIG. 7F), solubilizing up to 14±5% of the biomass.

Example 6

Biofuel Production: FAEE Production Pathway

The next step was to test biofuel production directly from IL-treated plant biomass to explore the feasibility of using *E. coli* in a consolidated bioprocess. Engineered plant biomass consumption capabilities were combined with pathways that produce alcohols, linear hydrocarbons, or branched-chain hydrocarbons, taking advantage of the extensive synthesis capabilities of *E. coli* (Atsumi & Liao, *Current Opinion in Biotechnology* 19, 414 (2008)). A list of the genes involved in the pathways is shown in Table 10.

TABLE 10

| Gene Name | NCBI Gene ID/GenBank Accession Number | Full name | Source organism | Reference |
|---|---|---|---|---|
| fadD | 6061811 | Long chain fatty acid CoA-ligase | E. coli | Steen et al., Nature 463, 559 (2010) |
| atfA | 2879218 | Wax ester synthase | A. baylyi ADP1 | Steen et al., Nature 463, 559 (2010) |
| pdc | 3188496 | Pyruvate decarboxylase | Z. mobilis ZM4 | Steen et al., Nature 463, 559 (2010) |
| adhB | 3187659 | Alcohol dehydrogenase | Z. mobilis ZM4 | Steen et al., Nature 463, 559 (2010) |
| LtesA | 945127 | Thioesterase ("leaderless" tesA) | E. coli | Steen et al., Nature 463, 559 (2010) |
| crt | 1118895 | Crotonase | C. acetobutylicum | Atsumi et al., Metabolic Engineering 10, 305 (2008) |
| bcd | 1118894 | Butyryl-CoA dehydrogenase | C. acetobutylicum | Atsumi et al., Metabolic Engineering 10, 305 (2008) |
| etfB | 1118893 | Electron transport flavoprotein B | C. acetobutylicum | Atsumi et al., Metabolic Engineering 10, 305 (2008) |
| etfA | 1118892 | Electron transport flavoprotein A | C. acetylbutylicum | Atsumi et al., Metabolic Engineering 10, 305 (2008) |
| hbd | 1118891 | 3-hydroxybutyryl-CoA dehydrogenase | C. acetobutylicum | Atsumi et al., Metabolic Engineering 10, 305 (2008) |
| atoB | 946727 | Acetyl-CoA acetyltransferase | E. coli | Atsumi et al., Metabolic Engineering 10, 305 (2008) |
| adhE2 | AF321779.1 | Aldehyde/alcohol dehydrogenase | C. acetobutylicum | Atsumi et al., Metabolic Engineering 10, 305 (2008) |
| HMGS | 854913 | Hydroxymethyl glutaryl-CoA synthase | S. cerevisiae | Martin et al., Nature Biotechnology 21, 796 (2003) |
| HMGR | 851171 | Hydroxymethyl glutaryl-CoA reductase | S. cerevisiae | Martin et al., Nature Biotechnology 21, 796 (2003) |
| MK | 855248 | Mevalonate kinase | S. cerevisiae | Martin et al., Nature Biotechnology 21, 796 (2003) |
| PMK | 855260 | Phosphomevalonate kinase | S. cerevisiae | Martin et al., Nature Biotechnology 21, 796 (2003) |
| PMD | 855779 | Phosphomevalonate decarboxylase | S. cerevisiae | Martin et al., Nature Biotechnology 21, 796 (2003) |
| idi | 6062310 | Isopentenyl pyrophosphate isomerase | E. coli | Martin et al., Nature Biotechnology 21, 796 (2003) |
| PINE | AF543527 (Pt1); AF543528 (Pt5); AF543529 (Pt10); AF543530 (Pt30); AF543531 (Pt42) | Pinene synthase | P. taeda | Phillips et al., Archives of Biochemistry and Biophysics 411, 267 (2003) |
| GPPS | AF513112.1 | geranyl pyrophosphate synthase | A. grandis | Burke & Croteau, Archives of Biochemistry and Biophysics 405, 130 (2002) |

Biodiesel, typically made from chemically esterified plant oils, can be made in vivo in *E. coli* (Steen et al., *Nature* 463, 559 (2010)). A fatty acid ethyl ester (FAEE) production pathway, encoded on a single plasmid (pES120, FIG. 10; Table 10), was introduced into *E. coli* MG1655 strain lacking the acyl-CoA dehydrogenase gene fadE.

Construction of pES120 pLacUV5 was amplified using primers that add BglII (5') and XhoI (3') sites and digested with the restriction enzymes BglII and XhoI. The digested product was ligated into BglII-XhoI-digested plasmid pKS104 (Steen et al., *Nature* 463, 559 (2010)), producing plasmid pES104. The pdc and adhB genes from pKS13 (Steen et al., Nature 463, 559 (2010)) were amplified using primers pdc-bb-for and adhB-bb-rev and digested with the restriction enzymes BglII and XhoI. The digested product was ligated into BglII-XhoI-digested plasmid pES104, producing plasmid pES105. The previous pLacUV5 digested product was ligated into BglII-XhoI-digested plasmid pES105, producing pES106. LtesA (Steen et al., Nature 463, 559 (2010)) was amplified using the primers LtesA-bb-for and LtesA-bb-rev and digested with BglII and XhoI. The digested product was ligated into BglII-XhoI-digested plasmid pES106, producing plasmid pES107. The previous pLacUV5 digested product was ligated into BglII-XhoI-digested plasmid pES107, producing pES109. The gene atfA (Steen et al., Nature 463, 559 (2010)) was amplified using the primers atfA-bb-for and atfA-bb-rev and the product was subsequently digested with BglII and XhoI and ligated into BglII-XhoI-digested pES109, producing pES114. Finally, the 3-operon, 6-gene cassette was cloned into plasmid pBbE5k-RFP. Details about the primers are shown in Table 11.

Table 11 shows a list of primers used to construct pES120.

TABLE 11

| Primer Name | Primer Sequence | SEQ ID NO: |
|---|---|---|
| ltesA-bb-R | tatatCTCGAGattGGATCCttatgagtcatgatttactaaaggctgc | 92 |
| pdc-adhBB-F | tttttcGAATTCaccAGATCTCTGCAGTAGGAGGAATTAACC | 93 |
| pdc-adhBB-R | atatttCTCGAGattGGATCCttagaaagcgctcaggaagag | 94 |
| LtesA-bbF | tataGAATTCaccAGATCTaattcaaaggaggccatcct | 95 |
| pLacUV5-bbF | tataGAATTCaccAGATCTgagaggctttacactttatgcttc | 96 |
| pLacUV5-bbR | ttaaCTCGAGattGGATCCttcctttgaattcaattgttatccgc | 97 |
| atfA-bb-R | ttaaCTCGAGattGGATCCttaattggctgttttaatatcttcctgc | 98 |
| atfA-bb-F | tataGAATTCaccAGATCTactagtaaggaggaaacagaatgc | 99 |

Construction of E. coli Strain MG1655 ΔfadE

E. coli strain MG1655 ΔfadE was constructed using homologous recombination with the Lambda Red system (Datsenko & Wanner, Proceedings of the National Academy of Sciences of the United States of America 97, 6640 (2000)) using primers GEB040110-dFadE.f and GEB040110-dFadE.r (Table 12) to amplify the kanamycin resistance gene from the plasmid pKD13 with homology arms to the region nearby the fadE gene.

Table 12 shows the primers used to construct E. coli strain MG1655 ΔfadE.

TABLE 12

| Primer Name | Primer Sequence | SEQ ID NO: |
|---|---|---|
| GEB040110-dFadE.f | ATCCACTACAACCATATCATCACAAGTGGTC AGACCTCCTACAAGTAAGGattccggggatccgtcgac | 100 |
| GEB040110-dFadE.r | AATAATTAGCGGATAAAGAAACGGAGCCTTT CGGCTCCGTTATTCATTTAgtgtaggctggagctgc ttc | 101 |

Conversion of Switchgrass to FAEE

Three cultures of 5 mL MOPS-M9 medium containing either 5.5% sterilized washed switchgrass or no carbon source were prepared and inoculated 1/20 with cultures of MG1655 ΔfadE pES120 with either pXylan or pCellulose (or 1/10 with control pBbS7a culture) grown for 24 hours in LB medium supplemented with 100 μg/mL carbenicillin and 100 μg/mL kanamycin. Cultures were grown at 37° C. for 92 hours, at which point FAEE production was induced by addition of IPTG to a final concentration of 50 μM. The production cultures were left at room temperature for 4 hours and returned to 37° C. for 96 hours of production time.

Whole production cultures were transferred to 15 mL sterile Falcon tubes and centrifuged, and 200 μL sample of the supernatant were taken for cellulase and xylanase measurements. Free fatty acid ethyl esters, and free fatty acids, were measured largely as described in Steen et al., Nature 463, 559 (2010).

Results: FAEE Production from Switchgrass

Figure 11:
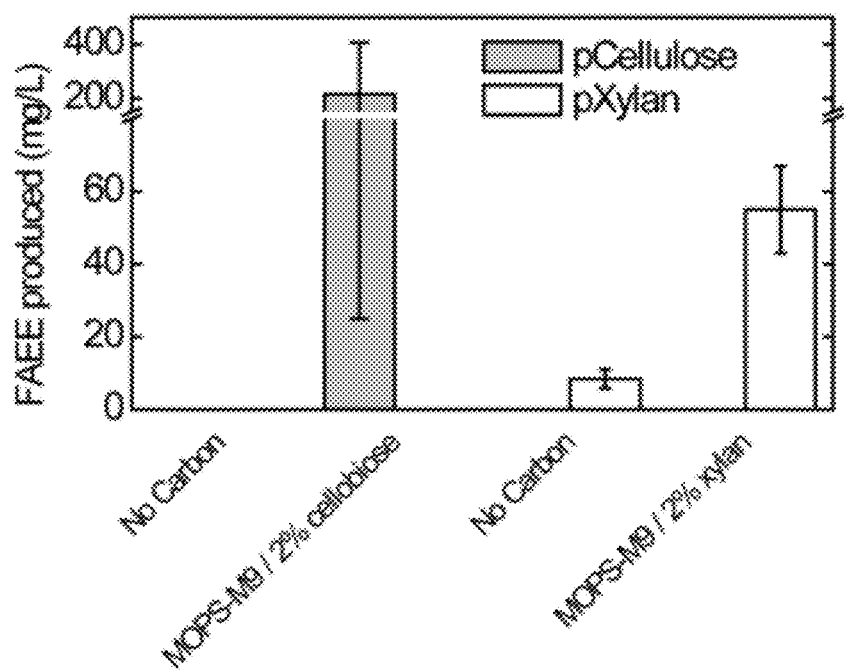
FIG. 11 shows production of FAEE from either cellobiose or xylan by *E. coli* MG1655 ΔfadE pES120 bearing either pCellulose or pXylan, respectively, indicating that each strain was capable of producing FAEE from its substrate. Error bars represent standard deviation of biological triplicates. Overnight cultures grown in LB medium were inoculated 1/10 into 5 mL of MOPS-M9/2% cellobiose or beechwood xylan medium or medium with no carbon source. Cultures were induced with 50 μM IPTG after 1-2 days of growth, and produced FAEE were extracted 2 days after induction. All media were supplemented with 100 μg/mL carbenicillin and kanamycin. No FAEE were produced by *E. coli* MG1655 ΔfadE pES120 bearing pCellulose in medium without cellobiose.
Figure 12:
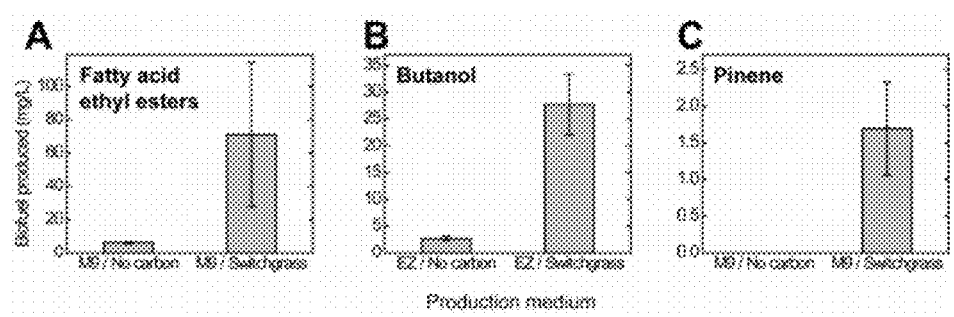
FIG. 12 shows conversion of IL-treated switchgrass into fatty acid ethyl esters (A), butanol (B), and pinene (C) by co-cultures of cellulose- and xylan-consuming *E. coli*. Error bars represent standard deviation of biological triplicates.

E. coli MG1655 ΔfadE pES120 bearing pXylan or pCellulose produced FAEE from xylan or cellobiose, respectively (FIG. 11), indicating that both strains are capable of FAEE production from their substrates. In order to produce FAEE from plant biomass, a co-culture of both strains was grown in minimal medium containing 5.5% w/v IL-treated switchgrass. The co-culture produced 71±43 mg/L of FAEE, well above the no-carbon control (6.1±0.5 mg/L; FIG. 12A) and the noncellulolytic E. coli control (4±3 mg/L), indicating production of FAEE directly from switchgrass.

Cellulase and xylanase activities were also tested. The protocol for the cellulase activity assay was as described in Example 1. A similar protocol was followed to assay for xylanase activity, except the S-ACMCL (used in cellulase activity assay) was substituted with azo-beechwood xylan (S-AXBL; Megazyme, Bray, Ireland).

Example 7

Biofuel Production: Butanol Production Pathway

Figure 10:
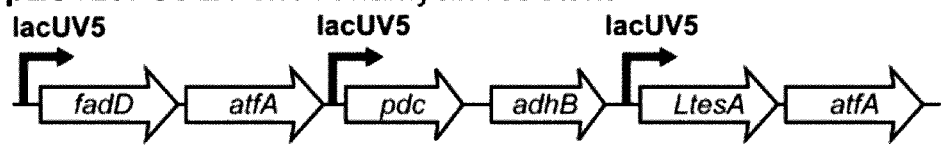
FIG. 10 shows gene schematics of plasmids used to encode biofuel production pathways.
Figure 10:
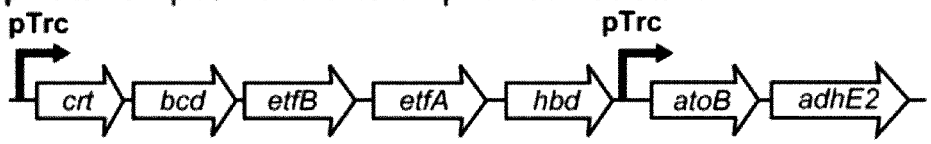
Figure 10:
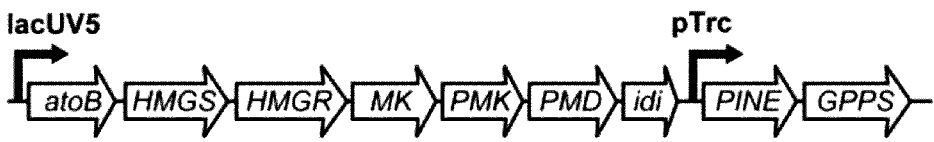

Butanol has been proposed as a gasoline replacement as it is fully compatible with existing internal combustion engines. A heterologous pathway for butanol production has been demonstrated in E. coli (Atsumi et al., Metabolic Engineering 10, 305 (2008)). The complete production pathway was constructed and encoded on a single plasmid (pButanol; FIG. 10; Table 10) and inserted into an E. coli DH1 strain lacking the alcohol dehydrogenase gene adhE.

Construction of pButanol

The C. acetobutylicum butyryl-CoA biosynthetic operon—crt, hbd, etfAB, hbd genes—was amplified from C.

acetobutylicum ATCC824 genomic DNA (ATCC) using primers F76/F73. The C. acetobutylicum alcohol dehydrogenase adhE2 gene was amplified using primers F72/F74; primer F72 included a synthetic ribosome binding site with an estimated translation initiation rate of 50,000 (arbitrary units) (Salis et al., Nature Biotechnology 27, 946 (2009)). The vector backbone containing a p15A origin, chloramphenicol selective marker, P$_{trc}$ promoter and gene encoding for LacIQ was amplified using primers F75/F77. The three PCR products were assembled using SLIC, producing plasmid pBMO49. A copy of E. coli atoB and an additional P$_{trc}$ promoter were inserted before adhE2. The gene atoB was PCR amplified from the E. coli chromosome using primers F92/F93; primer F92 contained a synthetic ribosome binding site with estimated translation initiation rate of 100,000 (arbitrary units). The P$_{trc}$ promoter was PCR-amplified using primers F90/F91. The vector backbone was digested with restriction enzymes BglII and BamHI, and subsequently assembled with the P$_{trc}$ and atoB PCR products using the SLIC protocol, producing plasmid pBMO50, referred to here as pButanol. Details about the primers are shown in Table 13.

Table 13 shows a list of primers used to construct pButanol.

TABLE 13

| Primer Name | Primer Sequence | SEQ ID NO: |
|---|---|---|
| F72 | attaatacgcgagttaaggagtacaggagcatgaaggtgaccaatcagaaagaactgaa | 102 |
| F73 | tactccttaactcgcgtattaatttggatccttattttgaataatcgtagaaaccttttc | 103 |
| F74 | atctacattaagagcttttgaagatctgaagcttgggcccgaacaaaaac | 104 |
| F75 | gttttgttcgggcccaagcttcagatcttcaaaagctcttaatgtagat | 105 |
| F76 | ttgtg agcggataac aatttcacaccagcaggacgcactgagggcccatg | 106 |
| F77 | catgggccctcagtgcgtcctgctggtgtgaaattgttatccgctcacaa | 107 |
| F90 | tttctacgattattcaaaataaggatcccgactgcacggtgcaccaatgcttctggcg | 108 |
| F91 | acctacctccttatttcaattttttcgatgaattgttatccgctcacaattccacacatt | 109 |
| F92 | aaaattg aaataaggaggtaggtagtaatgaaaaattgtgtcatcgtcagtgcggtacg | 110 |
| F93 | tgtactccttaactcgcgtattaatttgttaattcaaccgttcaatcaccatcgcaat | 111 |

Construction of E. coli Strain DH1 ΔadhE

E. coli strain DH1 ΔadhE was constructed with the Lambda Red system using primers F9 and F10* (Table 14) to amplify the kanamycin resistance gene from pKD13 with homology arms targeting the adhE gene.

Table 14 shows the primers used to construct E. coli strain DH1 ΔadhE.

TABLE 14

| Primer Name | Primer Sequence | SEQ ID NO: |
|---|---|---|
| F9 | gccgtttatgttgccagacagcgctactgagtgtaggctggagctgcttc gaagttccta | 112 |
| F10* | acattatcaggagagcattactgtcaaacatgagaattaattccggggat | 113 |

Conversion of Switchgrass to Butanol

Twelve cultures of 5 mL EZ-Rich medium (Teknova) were prepared as described by the manufacturer with 100 μg/mL carbenicillin and 30 μg/mL chloramphenicol and without glucose. Six of the cultures contained 3.3% (w/v) washed, IL-treated switchgrass. E. coli DH1 ΔadhE pButanol carrying pCelluose or pXylan was grown in LB medium containing 100 μg/mL carbenicillin and 30 μg/mL chloramphenicol for 38 or 25 hours, respectively, at 37° C. Biomass and null media were inoculated with 0.25 mL of each culture (0.5 mL total inoculum size). The cultures were moved to 37° C. for 6.5 hours, after which 2 mL of EZ-Rich salts (to final concentration, including original formulation, of 2x) was added to the cultures. Cultures were subsequently incubated at 30° C. for 30 minutes, after which they were induced by addition of IPTG to 200 μM and sealed with parafilm, creating a microaerobic environment, and returned to 30° C. for 96 hours.

Butanol was extracted from 750 μL of the culture by adding 750 μL ethyl acetate and vigorously mixing the phases. The ethyl acetate contained 0.05% pentanol as an internal standard. The ethyl acetate phase was analyzed with gas chromatography on a Focus GC (Thermo Scientific, Waltham, Mass., USA) equipped with a Triplus autosampler and a flame ionization detector maintained at 250° C. Separation occurred on a TR-WAX capillary column (Agilent Technologies, Santa Clara, Calif., USA) with helium as the carrier gas at 300 kPa using the following program: initial temperature 45° C. for 15 minutes, followed by a 15° C./minute ramp to 90° C., followed by a 30° C. ramp to 120° C.

Results: Butanol Production from Switchgrass

Figure 13:
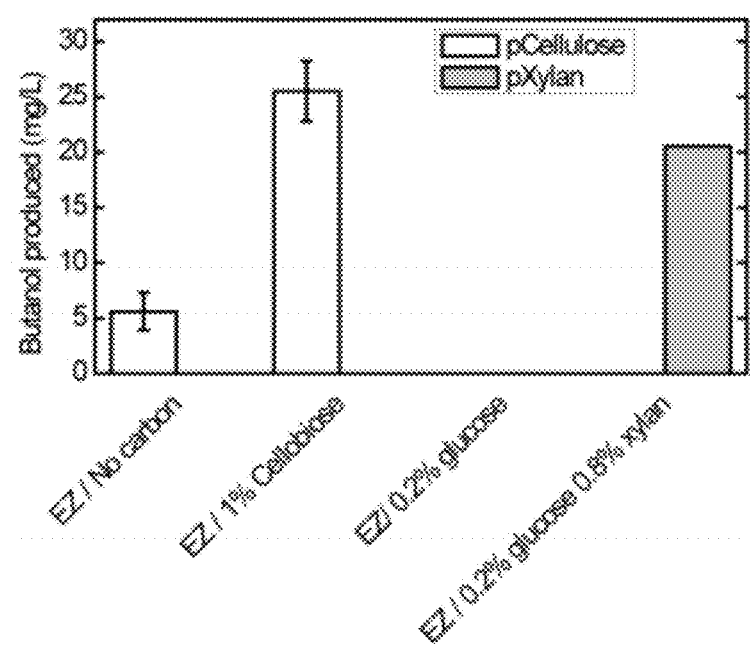
FIG. 13 shows butanol produced by *E. coli* DH1 ΔadhE pButanol strains bearing either pCellulose or pXylan, from EZ-Rich medium containing either 1% cellobiose or 1% beechwood xylan, indicating that each strain is capable of producing butanol from its substrate. Production media were inoculated 1/20 from monocultures grown in LB medium, and grown for several hours before induction with 200 μM IPTG. After induction, the tubes were sealed with parafilm and moved to 30° C. Butanol was extracted after 2 days of production. All media were supplemented with 100 μg/mL carbenicillin and 30 μg/mL chloramphenicol. Error bars (pCellulose only) represent standard deviation of biological triplicates. No butanol was detected in the EZ/0.2% glucose culture.

When bearing either pXylan or pCellulose, E. coli DH1 ΔadhE pButanol produced butanol from either xylan or cellobiose, respectively (FIG. 13). A co-culture of both strains yielded 28±5 mg/L butanol from defined rich medium containing 3.3% w/v IL-treated switchgrass as the main carbon source (FIG. 12B). A control strain lacking pXylan or pCellulose produced 8±2 mg/L butanol from 3.3% switchgrass.

Example 8

Biofuel Production: Pinene Production Pathway

Figure 14:
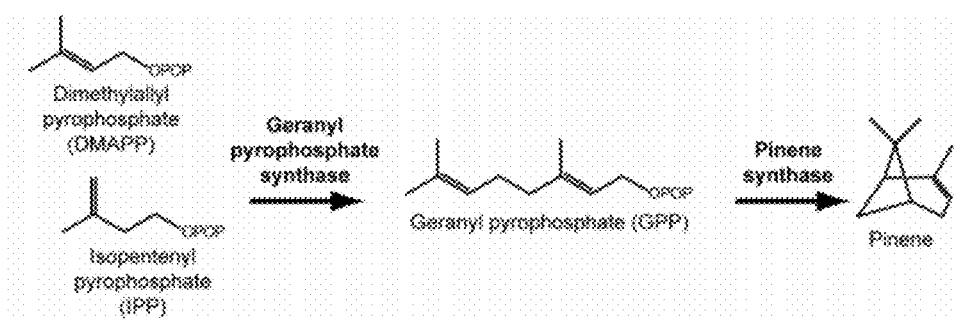
FIG. 14 shows the pinene synthesis pathway. Pinene is made by cyclization of geranyl pyrophosphate (GPP) using a pinene synthase enzyme from the loblolly pine *Pinus taeda* (Phillips et al., *Archives of Biochemistry and Biophysics* 411, 267 (2003)). GPP is in turn produced from isopentenyl pyrophosphate (IPP) and dimethylallyl pyrophosphate (DMAPP) by a geranyl pyrophosphate synthase (GPPS) from the fir tree *Abies grandis* (FIG. 12C) (Burke & Croteau, *Archives of Biochemistry and Biophysics* 405, 130 (2002)). The pPinene plasmid also includes a synthesis pathway for the GPPS precursors IPP and DMAPP (Martin et al., *Nature Biotechnology* 21, 796 (2003)).

Production of the monoterpene pinene, an immediate chemical precursor to a potential jet fuel (Keseler et al., *Nucleic Acids Research* 37, D464 (2009)), directly from switchgrass was tested. The pinene synthesis pathway (FIG. 14; Table 10) was encoded on a single plasmid (pPinene; FIG. 10) and introduced into *E. coli* MG1655.

Construction of pPinene pBbA5c-MevT-MBI was prepared by ligation of pBbA5c-MevT vector (BamHI/XhoI) and BglBrick compatible MBI insert (BglII/XhoI) by standard BglBrick cloning strategy using compatible BglII and BamHI restriction sites. Individual genes in the mevalonate pathway were PCR-amplified from pMevT and pMBI (Martin et al., *Nature Biotechnology* 21, 796 (2003)) with primers containing EcoRI and BglII sites at the 5'-end and BamHI and XhoI sites at the 3'-end of each gene. The BglBrick restriction sites found in each gene were removed by site-specific mutagenesis. Both MevT and MBI were constructed separately by sequential standard BglBrick ligation in pBbA5c vector (BglBricked vector with p15A origin, $P_{lacUV5}$ promoter, and chloramphenicol resistance), and combined to generate pBbA5c-MevT-MBI.

The geranyl pyrophosphate synthase (GPPS) from *Abies grandis* and the pinene synthase (PS) from *Pinus tadea* were codon-optimized for *E. coli* and synthesized (Genescript). The GPPS and the PS were cloned into pTRC99, plastid signal peptides removed, between NcoI and XmaI using primer pairs PPY630/PPY608 and PPY642/PPY643, respectively, to generate plasmids pGPPS and pPS. The plasmid pPS-GPPS was constructed by amplifying the GPPS from pGPPS using primer pair PPY674/PPY652 and introducing it into pPS between BamHI and HindIII via SLIC. The GPPS and PS genes with the $P_{TRC}$ promoter were amplified from pPS-GPPS using primers GB090110-PinepTrc. For and GB082010-Pine.Revseq, digested with BglII and XhoI, and ligated into a BamHI-XhoI digested pBbA5c-MevT-MBI to create pPinene. Details about the primers are shown in Table 15.

Table 15 shows a list of primers used to construct pPinene.

TABLE 15

| Primer Name | Primer Sequence | SEQ ID NO: |
|---|---|---|
| 5'-end of BglBricked AtoB | ccgGAATTCaaaAGATCTtaggaggaatataaaATGaaaaattgtgtca | 114 |
| 3'-end of BglBricked AtoB | ccgCTCGAGtttGGATCCtcaattcaaccgttcaatcaccatcg | 115 |
| 5'-end of BglBricked HMGS | ccgGAATTCaaaAGATCTtgaattaaggaggacagctaaATGaaactctcaactaaactt | 116 |
| 3'-end of BglBricked HMGS | ccgCTCGAGtttGGATCCtcattattaacatcgtaggatcttcta | 117 |
| 5'-end of BglBricked HMGR | ccgGAATTCaaaAGATCTaaaataaggaggattacactATGgttttaaccaataaaacag | 118 |
| 3'-end of BglBricked HMGR | ccgCTCGAGtttGGATCCtcaggatttaatgcaggtgacg | 119 |
| 5'-end of BglBricked MK | ccgGAATTCaaaAGATCTaggaggttaattggATGtcattaccgttcttaacttctgcac | 120 |
| 3'-end of BglBricked MK | ccgCTCGAGtttGGATCCctatgaagtccatggtaaattcgtgtttcc | 121 |
| 5'-end of BglBricked PMK | ccgGAATTCaaaAGATCTtaaggaggatacccctATGtcagagttgagagccttcagtgcc | 122 |
| 3'-end of BglBricked PMK | ccgCTCGAGtttGGATCCctatttatcaagataagtttccggatc | 123 |
| 5'-end of BglBricked PMD | ccgGAATTCaaaAGATCTaggaggattatgagATGaccgtttacacagcatccgttaccg | 124 |
| 3'-end of BglBricked PMD | ccgCTCGAGtttGGATCCttattcctttggtagaccagtctttgcg | 125 |
| 5'-end of BglBricked idi | ccgGAATTCaaaAGATCTaggaggtaatgataATGcaaacggaacacgtcattttattg | 126 |
| 3'-end of BglBricked idi | ccgCTCGAGtttGGATCCttatttaagctgggtaaatgcagataatc | 127 |
| PPY-608 | cccgggttaattctgacgaaatgccacg | 128 |
| PPY-630 | ccatggaatttgacttcaacaaatac | 129 |
| PPY-642 | ccatggcgcgtcgtatcgcgggtcacc | 130 |
| PPY-643 | cccgggttacagcggaacggtttca | 131 |

TABLE 15-continued

| Primer Name | Primer Sequence | SEQ ID NO: |
|---|---|---|
| PPY-652 | ccgccaaaacagccaag | 132 |
| PPY-674 | ccgctgtaacccggggatccaattgtgagcggataacaatt | 133 |
| GB082010-Pine.Revseq | GTC CGC ACG TTT ACG GTA AG | 134 |
| GB090110-PinepTrc.For | taatcc AGATCT TGA CAG CTT ATC ATC GAC TGC ACG GT | 135 |

Conversion of Switchgrass to Pinene

Twelve cultures of 5 mL MOPS-M9 medium with 100 μg/mL carbenicillin and 30 μg/mL chloramphenicol, six of which contained 3.9% (w/v) washed switchgrass, were prepared. Three overnight cultures each of MG1655/pPinene carrying pBbS7a, pXylan or pCellulose were grown for 24 hours in LB medium with 100 μg/mL carbenicillin and 30 μg/mL chloramphenicol. 0.5 mL of pBbS7a culture or 0.25 mL of both pXylan and pCellulose was added to the switchgrass and null media, and the cultures were grown at 37° C. After 22 hours, pinene production was induced by addition of IPTG to 200 μM, 0.55 mL dodecane was added to trap the pinene, and the cultures were moved to 30° C. for 72 hours.

Identification and quantification of the microbially produced α-pinene were performed by gas chromatography/mass spectrometry (GC/MS) using authentic α-pinene (Acros Organics, Morris Plains, N.J., USA) of known concentration. After identifying the microbially produced pinene in MS full scan mode, m/z 136 and 121 were chosen for selective ion monitoring. The organic layer was analyzed by GC/MS (Polaris Q Trace GC Ultra) equipped with a TR-5MS capillary column (30 m×0.25 mm internal diameter, 0.25 μM film thickness) (Thermo Scientific). The gas chromatography program used was 70° C. for 1 minute, then ramping 35° C. min.$^{-1}$ to 150° C., and 40° C. min.$^{-1}$ to 250° C.

Results: Pinene Production from Switchgrass

Figure 15:
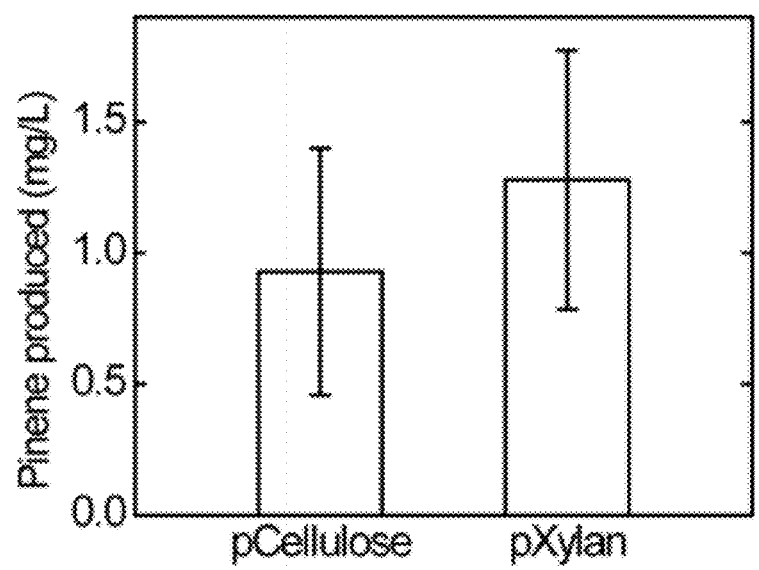
FIG. 15 shows pinene produced by *E. coli* MG1655 pPinene bearing either pCellulose or pXylan from cellobiose or xylan, respectively. Overnight cultures were inoculated 1/10 into 5 mL MOPS-M9 medium containing 2% cellobiose or beechwood xylan, or no carbon source at all, grown overnight, and induced with 200 mM IPTG. A dodecane overlay was applied and the cultures were moved to 30° C. for 3 days before pinene was extracted from the dodecane. All media were supplemented with 100 μg/mL carbenicillin and 30 μg/mL chloramphenicol. No pinene was produced in medium without an added carbon source. Error bars represent standard deviation of biological triplicates.

The two plasmids pXylan and pCellulose were combined into separate strains of E. coli MG1655 pPinene. The results confirmed that each strain was capable of producing pinene from either xylan or cellobiose, respectively (FIG. 15).

The strains were inoculated as a co-culture in MOPS-M9 medium containing either 3.9% IL-treated switchgrass or no carbon source. The pinene pathway yielded 1.7±0.6 mg/L pinene from switchgrass (FIG. 12C). No pinene was produced from a culture grown in MOPS-M9 medium without a carbon source or from switchgrass medium inoculated with a strain lacking pXylan or pCellulose.

What is claimed is:

1. A method for producing butanol from a biomass polymer, comprising:
 a) providing a host cell, wherein the host cell does not naturally produce butanol and comprises one or more heterologous recombinant nucleic acids encoding a crotonase, a butyryl-coA dehydrogenase, an electron transport flavoprotein B, an electron transport flavoprotein A, a 3-hydroxybutyryl-coA dehydrogenase, an acetyl-coA acetyltransferase, or an aldehyde/alcohol dehydrogenase, and one or more biomass polymer-degrading enzymes, wherein at least one of the one or more biomass polymer-degrading enzymes is secreted from the host cell,
 b) culturing the host cell in a medium to form a culture such that the one or more recombinant nucleic acids are expressed in the cell, wherein the medium comprises a biomass polymer as a carbon source for the host cell, and
 c) extracting butanol from the culture.

2. The method of claim 1, wherein the host cell comprises an endogenous nucleic acid encoding an alcohol dehydrogenase.

3. The method of claim 2, wherein the host cell is modified such that expression of the alcohol dehydrogenase is attenuated relative to the level of expression in a non-modified cell.

4. The method of claim 1, wherein the host cell is selected from the group consisting of a bacterial cell, a fungal cell, a yeast cell, a plant cell, an animal, and a human cell.

5. The method of claim 1, wherein the crotonase is crt from *C. acetylbutylicum*, the butyryl-coA dehydrogenase is bcd from *C. acetylbutylicum*, the electron transport flavoprotein B is etfB from *C. acetylbutylicum*, the electron transport flavoprotein A is etfA from *C. acetylbutylicum*, the 3-hydroxybutyryl-coA dehydrogenase is hbd from *C. acetylbutylicum*, the acetyl-coA acetyltransferase is atoB from *E. coli*, and the aldehyde/alcohol dehydrogenase is adhE2 from *C. acetylbutylicum*.

6. The method of claim 1, wherein the biomass polymer is cellulose.

7. The method of claim 6, wherein the one or more biomass polymer-degrading enzymes are a cellulase and a β-glucosidase.

8. The method of claim 1, wherein the biomass polymer is hemicellulose.

9. The method of claim 8, wherein the hemicellulose is xylan.

10. The method of claim 9, wherein the one or more biomass polymer-degrading enzymes are an endoxylanase and a xylobiosidase.

11. The method of claim 1, wherein the host cell is an *E. coli* cell.

12. The method of claim 1, wherein the biomass-polymer degrading enzyme is encoded by one or more recombinant nucleic acids.

13. The method of claim 1, wherein the host cell comprises one or more recombinant nucleic acids encoding a crotonase, a butyryl-coA dehydrogenase, an electron transport flavoprotein B, an electron transport flavoprotein A, a 3-hydroxybutyryl-coA dehydrogenase, an acetyl-coA acetyltransferase, and an aldehyde/alcohol dehydrogenase.

* * * * *

SEQUENCE LISTING

```
<160> NUMBER OF SEQ ID NOS: 135

<210> SEQ ID NO 1
<211> LENGTH: 40
<212> TYPE: DNA
<213> ORGANISM: Artificial Sequence
<220> FEATURE:
<223> OTHER INFORMATION: Synthetic Construct

<400> SEQUENCE: 1
agctaaagat ctagcaggag gaaaaaaaaa tgactatgac                    40

<210> SEQ ID NO 2
<211> LENGTH: 45
<212> TYPE: DNA
<213> ORGANISM: Artificial Sequence
<220> FEATURE:
<223> OTHER INFORMATION: Synthetic Construct

<400> SEQUENCE: 2
tcattactcg agttaggatc cgctgccctt agttttcaga tcatt              45

<210> SEQ ID NO 3
<211> LENGTH: 40
<212> TYPE: DNA
<213> ORGANISM: Artificial Sequence
<220> FEATURE:
<223> OTHER INFORMATION: Synthetic Construct

<400> SEQUENCE: 3
ctacggaatt catgagatct attaaccaaa atgcaaccta                    40
```

```
<210> SEQ ID NO 4
<211> LENGTH: 41
<212> TYPE: DNA
<213> ORGANISM: Artificial Sequence
<220> FEATURE:
<223> OTHER INFORMATION: Synthetic Construct

<400> SEQUENCE: 4
gtagtcctcg agtttggatc cgttgttgta cgcctcttgc a            41

<210> SEQ ID NO 5
<211> LENGTH: 40
<212> TYPE: DNA
<213> ORGANISM: Artificial Sequence
<220> FEATURE:
<223> OTHER INFORMATION: Synthetic Construct

<400> SEQUENCE: 5
ctacggaatt catgagatct atccgcgata tctcctccaa              40

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6
gtagtcctcg agtttggatc ctttctttc tacggcgtgt a             41

<210> SEQ ID NO 7
<211> LENGTH: 40
<212> TYPE: DNA
<213> ORGANISM: Artificial Sequence
<220> FEATURE:
<223> OTHER INFORMATION: Synthetic Construct

<400> SEQUENCE: 7
ctacggaatt catgagatct atccgcagcc cagcgtccgc              40

<210> SEQ ID NO 8
<211> LENGTH: 41
<212> TYPE: DNA
<213> ORGANISM: Artificial Sequence
<220> FEATURE:
<223> OTHER INFORMATION: Synthetic Construct

<400> SEQUENCE: 8
gtagtcctcg agtttggatc cggtgctgtc cttagtaccc a            41

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
ctacggaatt catgagatct cgtgagcaaa gccattatga              40

<210> SEQ ID NO 10
<211> LENGTH: 41
<212> TYPE: DNA
<213> ORGANISM: Artificial Sequence
<220> FEATURE:
```

<223> OTHER INFORMATION: Synthetic Construct

<400> SEQUENCE: 10
gtagtcctcg agtttggatc ccagataacg aatgatctgt t                41

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct

<400> SEQUENCE: 11
ctacggaatt catgagatct tggaacgcat ctgacgtacc                  40

<210> SEQ ID NO 12
<211> LENGTH: 41
<212> TYPE: DNA
<213> ORGANISM: Artificial Sequence
<220> FEATURE:
<223> OTHER INFORMATION: Synthetic Construct

<400> SEQUENCE: 12
gtagtcctcg agtttggatc ccttattatc tttcagcata a                41

<210> SEQ ID NO 13
<211> LENGTH: 40
<212> TYPE: DNA
<213> ORGANISM: Artificial Sequence
<220> FEATURE:
<223> OTHER INFORMATION: Synthetic Construct

<400> SEQUENCE: 13
ctacggaatt catgagatct aatgcactga ccgcaactcc                  40

<210> SEQ ID NO 14
<211> LENGTH: 41
<212> TYPE: DNA
<213> ORGANISM: Artificial Sequence
<220> FEATURE:
<223> OTHER INFORMATION: Synthetic Construct

<400> SEQUENCE: 14
gtagtcctcg agtttggatc caacaccagt gcttttcttt t                41

<210> SEQ ID NO 15
<211> LENGTH: 40
<212> TYPE: DNA
<213> ORGANISM: Artificial Sequence
<220> FEATURE:
<223> OTHER INFORMATION: Synthetic Construct

<400> SEQUENCE: 15
ctacggaatt catgagatct acttctactc tgaaagccgc                  40

<210> SEQ ID NO 16
<211> LENGTH: 41
<212> TYPE: DNA
<213> ORGANISM: Artificial Sequence
<220> FEATURE:
<223> OTHER INFORMATION: Synthetic Construct

<400> SEQUENCE: 16
gtagtcctcg agtttggatc caaccagcag cgcggaacga c                41

```
<210> SEQ ID NO 17
<211> LENGTH: 40
<212> TYPE: DNA
<213> ORGANISM: Artificial Sequence
<220> FEATURE:
<223> OTHER INFORMATION: Synthetic Construct

<400> SEQUENCE: 17
ctacggaatt catgagatct ggtttcggct ggaacctggg                           40

<210> SEQ ID NO 18
<211> LENGTH: 41
<212> TYPE: DNA
<213> ORGANISM: Artificial Sequence
<220> FEATURE:
<223> OTHER INFORMATION: Synthetic Construct

<400> SEQUENCE: 18
gtagtcctcg agtttggatc ccttcgccgc gttgatcagc g                        41

<210> SEQ ID NO 19
<211> LENGTH: 40
<212> TYPE: DNA
<213> ORGANISM: Artificial Sequence
<220> FEATURE:
<223> OTHER INFORMATION: Synthetic Construct

<400> SEQUENCE: 19
ctacggaatt catgagatct cacggcccag gtcacaaaaa                           40

<210> SEQ ID NO 20
<211> LENGTH: 41
<212> TYPE: DNA
<213> ORGANISM: Artificial Sequence
<220> FEATURE:
<223> OTHER INFORMATION: Synthetic Construct

<400> SEQUENCE: 20
gtagtcctcg agtttggatc ccaggtacgc ttccagaatg t                        41

<210> SEQ ID NO 21
<211> LENGTH: 40
<212> TYPE: DNA
<213> ORGANISM: Artificial Sequence
<220> FEATURE:
<223> OTHER INFORMATION: Synthetic Construct

<400> SEQUENCE: 21
ctacggaatt catgagatct gttttctcct attctatttc                           40

<210> SEQ ID NO 22
<211> LENGTH: 41
<212> TYPE: DNA
<213> ORGANISM: Artificial Sequence
<220> FEATURE:
<223> OTHER INFORMATION: Synthetic Construct

<400> SEQUENCE: 22
gtagtcctcg agtttggatc cgtccttgcc gttccacagc t                        41

<210> SEQ ID NO 23
<211> LENGTH: 30
<212> TYPE: DNA
<213> ORGANISM: Artificial Sequence
<220> FEATURE:
<223> OTHER INFORMATION: Synthetic Construct
```

```
<400> SEQUENCE: 23
attcatgaga tctatccgca gcccagcgtc                                    30

<210> SEQ ID NO 24
<211> LENGTH: 51
<212> TYPE: DNA
<213> ORGANISM: Artificial Sequence
<220> FEATURE:
<223> OTHER INFORMATION: Synthetic Construct

<400> SEQUENCE: 24
tcattactcg agttaggatc cttaggtgct gtccttagta cccaggatat t            51

<210> SEQ ID NO 25
<211> LENGTH: 50
<212> TYPE: DNA
<213> ORGANISM: Artificial Sequence
<220> FEATURE:
<223> OTHER INFORMATION: Synthetic Construct

<400> SEQUENCE: 25
ctaatgagtg agctaactta cattaattgt ttctccacct cgtctctgtg              50

<210> SEQ ID NO 26
<211> LENGTH: 53
<212> TYPE: DNA
<213> ORGANISM: Artificial Sequence
<220> FEATURE:
<223> OTHER INFORMATION: Synthetic Construct

<400> SEQUENCE: 26
tatctccttc ttaaaagatc ttttgaattc cagggacatc cttttatcat cgg          53

<210> SEQ ID NO 27
<211> LENGTH: 58
<212> TYPE: DNA
<213> ORGANISM: Artificial Sequence
<220> FEATURE:
<223> OTHER INFORMATION: Synthetic Construct

<400> SEQUENCE: 27
ctaatgagtg agctaactta cattaattga gtaaatttag gattaatcct ggaactttt    58

<210> SEQ ID NO 28
<211> LENGTH: 51
<212> TYPE: DNA
<213> ORGANISM: Artificial Sequence
<220> FEATURE:
<223> OTHER INFORMATION: Synthetic Construct

<400> SEQUENCE: 28
tatctccttc ttaaaagatc ttttgaattc tttttgcgcc tcgttatcat c            51

<210> SEQ ID NO 29
<211> LENGTH: 51
<212> TYPE: DNA
<213> ORGANISM: Artificial Sequence
<220> FEATURE:
<223> OTHER INFORMATION: Synthetic Construct

<400> SEQUENCE: 29
ctaatgagtg agctaactta cattaattga acccgacaga attagatgag a            51

<210> SEQ ID NO 30
<211> LENGTH: 49
```

<212> TYPE: DNA
<213> ORGANISM: Artificial Sequence
<220> FEATURE:
<223> OTHER INFORMATION: Synthetic Construct

<400> SEQUENCE: 30
tatctccttc ttaaaagatc ttttgaattc agttgttatc cgtgtgcgt     49

<210> SEQ ID NO 31
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
ctaatgagtg agctaactta cattaattgc accatttcaa ttcattaata ttttagtagc     60

<210> SEQ ID NO 32
<211> LENGTH: 60
<212> TYPE: DNA
<213> ORGANISM: Artificial Sequence
<220> FEATURE:
<223> OTHER INFORMATION: Synthetic Construct

<400> SEQUENCE: 32
tatctccttc ttaaaagatc ttttgaattc atctctaacc atatgattta aaacaaatc     60

<210> SEQ ID NO 33
<211> LENGTH: 53
<212> TYPE: DNA
<213> ORGANISM: Artificial Sequence
<220> FEATURE:
<223> OTHER INFORMATION: Synthetic Construct

<400> SEQUENCE: 33
ctaatgagtg agctaactta cattaattgt ctccaataat tatccataag ccg     53

<210> SEQ ID NO 34
<211> LENGTH: 51
<212> TYPE: DNA
<213> ORGANISM: Artificial Sequence
<220> FEATURE:
<223> OTHER INFORMATION: Synthetic Construct

<400> SEQUENCE: 34
tatctccttc ttaaaagatc ttttgaattc ttctaaccac tcctcgtgtt a     51

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35
ctaatgagtg agctaactta cattaattgt tgtcagttat catcttcggt tacg     54

<210> SEQ ID NO 36
<211> LENGTH: 49
<212> TYPE: DNA
<213> ORGANISM: Artificial Sequence
<220> FEATURE:
<223> OTHER INFORMATION: Synthetic Construct

<400> SEQUENCE: 36
tatctccttc ttaaaagatc ttttgaattc gcttcgacat ccttcgcaa          49

<210> SEQ ID NO 37
<211> LENGTH: 59
<212> TYPE: DNA
<213> ORGANISM: Artificial Sequence
<220> FEATURE:
<223> OTHER INFORMATION: Synthetic Construct

<400> SEQUENCE: 37
ctaatgagtg agctaactta cattaattgg cgtctataaa atttaataaa taatgacgc          59

<210> SEQ ID NO 38
<211> LENGTH: 53
<212> TYPE: DNA
<213> ORGANISM: Artificial Sequence
<220> FEATURE:
<223> OTHER INFORMATION: Synthetic Construct

<400> SEQUENCE: 38
tatctccttc ttaaaagatc ttttgaattc agcgttatct cgcgtaaatc aac          53

<210> SEQ ID NO 39
<211> LENGTH: 34
<212> TYPE: DNA
<213> ORGANISM: Artificial Sequence
<220> FEATURE:
<223> OTHER INFORMATION: Synthetic Construct

<400> SEQUENCE: 39
gaattcaaaa gatcttttaa gaaggagata taca          34

<210> SEQ ID NO 40
<211> LENGTH: 30
<212> TYPE: DNA
<213> ORGANISM: Artificial Sequence
<220> FEATURE:
<223> OTHER INFORMATION: Synthetic Construct

<400> SEQUENCE: 40
caattaatgt aagttagctc actcattagg          30

<210> SEQ ID NO 41
<211> LENGTH: 48
<212> TYPE: DNA
<213> ORGANISM: Artificial Sequence
<220> FEATURE:
<223> OTHER INFORMATION: Synthetic Construct

<400> SEQUENCE: 41
agctaaagat ctaggaggaa aaaatgaaa gatgatttcc ctcaacgc          48

<210> SEQ ID NO 42
<211> LENGTH: 39
<212> TYPE: DNA
<213> ORGANISM: Artificial Sequence
<220> FEATURE:
<223> OTHER INFORMATION: Synthetic Construct

<400> SEQUENCE: 42
tcattactcg agttaggatc cttaggggca ggcgacgtc          39

<210> SEQ ID NO 43
<211> LENGTH: 45
<212> TYPE: DNA
<213> ORGANISM: Artificial Sequence

```
<220> FEATURE:
<223> OTHER INFORMATION: Synthetic Construct

<400> SEQUENCE: 43
agctaaagat ctaggaggaa aaaaatgctg tggccaaaag tcacc                45

<210> SEQ ID NO 44
<211> LENGTH: 48
<212> TYPE: DNA
<213> ORGANISM: Artificial Sequence
<220> FEATURE:
<223> OTHER INFORMATION: Synthetic Construct

<400> SEQUENCE: 44
tcattactcg agttaggatc cttaaccaac aacaccaaat gttccatg             48

<210> SEQ ID NO 45
<211> LENGTH: 45
<212> TYPE: DNA
<213> ORGANISM: Artificial Sequence
<220> FEATURE:
<223> OTHER INFORMATION: Synthetic Construct

<400> SEQUENCE: 45
agctaaagat ctaggaggaa aaaaatgcac ttgtcctgca aaacc                45

<210> SEQ ID NO 46
<211> LENGTH: 45
<212> TYPE: DNA
<213> ORGANISM: Artificial Sequence
<220> FEATURE:
<223> OTHER INFORMATION: Synthetic Construct

<400> SEQUENCE: 46
tcattactcg agttaggatc cttactcggg acacgtaatc gtctg                45

<210> SEQ ID NO 47
<211> LENGTH: 47
<212> TYPE: DNA
<213> ORGANISM: Artificial Sequence
<220> FEATURE:
<223> OTHER INFORMATION: Synthetic Construct

<400> SEQUENCE: 47
agctaaagat ctaggaggaa aaaaatgaaa aaacgacatc cactggc              47

<210> SEQ ID NO 48
<211> LENGTH: 48
<212> TYPE: DNA
<213> ORGANISM: Artificial Sequence
<220> FEATURE:
<223> OTHER INFORMATION: Synthetic Construct

<400> SEQUENCE: 48
tcattactcg agttaggatc cttatttcat gagggattgg atgtcctg             48

<210> SEQ ID NO 49
<211> LENGTH: 38
<212> TYPE: DNA
<213> ORGANISM: Artificial Sequence
<220> FEATURE:
<223> OTHER INFORMATION: Synthetic Construct

<400> SEQUENCE: 49
attcatgaga tctatgaccg gtaagaaagc attcaacg                        38
```

<210> SEQ ID NO 50
<211> LENGTH: 45
<212> TYPE: DNA
<213> ORGANISM: Artificial Sequence
<220> FEATURE:
<223> OTHER INFORMATION: Synthetic Construct

<400> SEQUENCE: 50
tcattactcg agttaggatc cttattcacg cagacgggat gggtc            45

<210> SEQ ID NO 51
<211> LENGTH: 42
<212> TYPE: DNA
<213> ORGANISM: Artificial Sequence
<220> FEATURE:
<223> OTHER INFORMATION: Synthetic Construct

<400> SEQUENCE: 51
taatccagat ctaggaggaa aaaaaatgc ccacccacca cc                42

<210> SEQ ID NO 52
<211> LENGTH: 51
<212> TYPE: DNA
<213> ORGANISM: Artificial Sequence
<220> FEATURE:
<223> OTHER INFORMATION: Synthetic Construct

<400> SEQUENCE: 52
ataccactcg agtttggatc cttatttcaa acgttggctg atgtaactat c      51

<210> SEQ ID NO 53
<211> LENGTH: 46
<212> TYPE: DNA
<213> ORGANISM: Artificial Sequence
<220> FEATURE:
<223> OTHER INFORMATION: Synthetic Construct

<400> SEQUENCE: 53
taatccagat ctaggaggaa aaaaaatgc gtccactaac catccg             46

<210> SEQ ID NO 54
<211> LENGTH: 41
<212> TYPE: DNA
<213> ORGANISM: Artificial Sequence
<220> FEATURE:
<223> OTHER INFORMATION: Synthetic Construct

<400> SEQUENCE: 54
ataccactcg agtttggatc cttacggcag cgccctatac a                 41

<210> SEQ ID NO 55
<211> LENGTH: 51
<212> TYPE: DNA
<213> ORGANISM: Artificial Sequence
<220> FEATURE:
<223> OTHER INFORMATION: Synthetic Construct

<400> SEQUENCE: 55
taatccagat ctaggaggaa aaaaaatgt ataagcgtat tttggccggt a       51

<210> SEQ ID NO 56
<211> LENGTH: 46
<212> TYPE: DNA
<213> ORGANISM: Artificial Sequence
<220> FEATURE:
<223> OTHER INFORMATION: Synthetic Construct

```
<400> SEQUENCE: 56
ataccactcg agttaggatc cttactattt caagcgtgtc agcgtc                    46

<210> SEQ ID NO 57
<211> LENGTH: 54
<212> TYPE: DNA
<213> ORGANISM: Artificial Sequence
<220> FEATURE:
<223> OTHER INFORMATION: Synthetic Construct

<400> SEQUENCE: 57
taatccagat ctaggaggaa aaaaaaatga aaaatacct atggctttgc ttgc             54

<210> SEQ ID NO 58
<211> LENGTH: 44
<212> TYPE: DNA
<213> ORGANISM: Artificial Sequence
<220> FEATURE:
<223> OTHER INFORMATION: Synthetic Construct

<400> SEQUENCE: 58
ataccactcg agtttggatc cttacaccag gcattgtcca tcgg                       44

<210> SEQ ID NO 59
<211> LENGTH: 47
<212> TYPE: DNA
<213> ORGANISM: Artificial Sequence
<220> FEATURE:
<223> OTHER INFORMATION: Synthetic Construct

<400> SEQUENCE: 59
taatccagat ctaggaggaa aaaaaaatga aattgacaag cctggcg                    47

<210> SEQ ID NO 60
<211> LENGTH: 51
<212> TYPE: DNA
<213> ORGANISM: Artificial Sequence
<220> FEATURE:
<223> OTHER INFORMATION: Synthetic Construct

<400> SEQUENCE: 60
ataccactcg agtttggatc cttattcatt gacatcaaca acattttgcc c               51

<210> SEQ ID NO 61
<211> LENGTH: 58
<212> TYPE: DNA
<213> ORGANISM: Artificial Sequence
<220> FEATURE:
<223> OTHER INFORMATION: Synthetic Construct

<400> SEQUENCE: 61
taatccagat ctaggaggaa aaaaaaatgt ctacagaaaa tgaagttgtt gattacaa        58

<210> SEQ ID NO 62
<211> LENGTH: 55
<212> TYPE: DNA
<213> ORGANISM: Artificial Sequence
<220> FEATURE:
<223> OTHER INFORMATION: Synthetic Construct

<400> SEQUENCE: 62
ataccactcg agttaggatc cttactaatc acgataggga tgaatcgttt taatt           55

<210> SEQ ID NO 63
```

<211> LENGTH: 47
<212> TYPE: DNA
<213> ORGANISM: Artificial Sequence
<220> FEATURE:
<223> OTHER INFORMATION: Synthetic Construct

<400> SEQUENCE: 63
taatccagat ctaggaggaa aaaaaatga aattgacaag cctggcg                    47

<210> SEQ ID NO 64
<211> LENGTH: 51
<212> TYPE: DNA
<213> ORGANISM: Artificial Sequence
<220> FEATURE:
<223> OTHER INFORMATION: Synthetic Construct

<400> SEQUENCE: 64
ataccactcg agtttggatc cttattcatt gacatcaaca acattttgcc c              51

<210> SEQ ID NO 65
<211> LENGTH: 47
<212> TYPE: DNA
<213> ORGANISM: Artificial Sequence
<220> FEATURE:
<223> OTHER INFORMATION: Synthetic Construct

<400> SEQUENCE: 65
taatccagat ctaggaggaa aaaaaatgc cattaccact gcgacat                    47

<210> SEQ ID NO 66
<211> LENGTH: 48
<212> TYPE: DNA
<213> ORGANISM: Artificial Sequence
<220> FEATURE:
<223> OTHER INFORMATION: Synthetic Construct

<400> SEQUENCE: 66
ataccactcg agtttggatc cttaaactat gggttggata ctgccatc                  48

<210> SEQ ID NO 67
<211> LENGTH: 48
<212> TYPE: DNA
<213> ORGANISM: Artificial Sequence
<220> FEATURE:
<223> OTHER INFORMATION: Synthetic Construct

<400> SEQUENCE: 67
taatccagat ctaggaggaa aaaaaatgt tagatgcaac ccgtaggg                   48

<210> SEQ ID NO 68
<211> LENGTH: 40
<212> TYPE: DNA
<213> ORGANISM: Artificial Sequence
<220> FEATURE:
<223> OTHER INFORMATION: Synthetic Construct

<400> SEQUENCE: 68
ataccactcg agtttggatc cttacgttga cgagcgcgcc                           40

<210> SEQ ID NO 69
<211> LENGTH: 52
<212> TYPE: DNA
<213> ORGANISM: Artificial Sequence
<220> FEATURE:
<223> OTHER INFORMATION: Synthetic Construct

<400> SEQUENCE: 69

```
taatccagat ctaggaggaa aaaaaaatgt tcaaacctgt ttctatccga cg        52
```

<210> SEQ ID NO 70
<211> LENGTH: 44
<212> TYPE: DNA
<213> ORGANISM: Artificial Sequence
<220> FEATURE:
<223> OTHER INFORMATION: Synthetic Construct

<400> SEQUENCE: 70

```
ataccactcg agtttggatc cttacttaac caacggcgtc acct                 44
```

<210> SEQ ID NO 71
<211> LENGTH: 47
<212> TYPE: DNA
<213> ORGANISM: Artificial Sequence
<220> FEATURE:
<223> OTHER INFORMATION: Synthetic Construct

<400> SEQUENCE: 71

```
taatccagat ctaggaggaa aaaaaaatgc cgctaaaaac gctagcc              47
```

<210> SEQ ID NO 72
<211> LENGTH: 43
<212> TYPE: DNA
<213> ORGANISM: Artificial Sequence
<220> FEATURE:
<223> OTHER INFORMATION: Synthetic Construct

<400> SEQUENCE: 72

```
ataccactcg agttaggatc cttagggtga ctgcctgaca tgc                  43
```

<210> SEQ ID NO 73
<211> LENGTH: 47
<212> TYPE: DNA
<213> ORGANISM: Artificial Sequence
<220> FEATURE:
<223> OTHER INFORMATION: Synthetic Construct

<400> SEQUENCE: 73

```
taatccagat ctaggaggaa aaaaaaatgc caaacctgat caacccg              47
```

<210> SEQ ID NO 74
<211> LENGTH: 52
<212> TYPE: DNA
<213> ORGANISM: Artificial Sequence
<220> FEATURE:
<223> OTHER INFORMATION: Synthetic Construct

<400> SEQUENCE: 74

```
ataccactcg agtttggatc cttattttgt actctgtttg tgtgtcacta ag        52
```

<210> SEQ ID NO 75
<211> LENGTH: 48
<212> TYPE: DNA
<213> ORGANISM: Artificial Sequence
<220> FEATURE:
<223> OTHER INFORMATION: Synthetic Construct

<400> SEQUENCE: 75

```
taatccagat ctaggaggaa aaaaaaatgg acgctgtctt tttttcgg             48
```

<210> SEQ ID NO 76
<211> LENGTH: 38
<212> TYPE: DNA

```
<213> ORGANISM: Artificial Sequence
<220> FEATURE:
<223> OTHER INFORMATION: Synthetic Construct

<400> SEQUENCE: 76
ataccactcg agtttggatc cttacgcacc gcgcacca                              38

<210> SEQ ID NO 77
<211> LENGTH: 48
<212> TYPE: DNA
<213> ORGANISM: Artificial Sequence
<220> FEATURE:
<223> OTHER INFORMATION: Synthetic Construct

<400> SEQUENCE: 77
taatccagat ctaggaggaa aaaaaaatga caacctccct gaattccc                  48

<210> SEQ ID NO 78
<211> LENGTH: 45
<212> TYPE: DNA
<213> ORGANISM: Artificial Sequence
<220> FEATURE:
<223> OTHER INFORMATION: Synthetic Construct

<400> SEQUENCE: 78
ataccactcg agtttggatc cttacttggc ggctttttta acccg                      45

<210> SEQ ID NO 79
<211> LENGTH: 42
<212> TYPE: DNA
<213> ORGANISM: Artificial Sequence
<220> FEATURE:
<223> OTHER INFORMATION: Synthetic Construct

<400> SEQUENCE: 79
attcatgaga tctatgaaaa ctgaaaaacg ttacctggtt cc                         42

<210> SEQ ID NO 80
<211> LENGTH: 53
<212> TYPE: DNA
<213> ORGANISM: Artificial Sequence
<220> FEATURE:
<223> OTHER INFORMATION: Synthetic Construct

<400> SEQUENCE: 80
tcattactcg agttaggatc cttattcatc tttaccttcg atagtgatga tac             53

<210> SEQ ID NO 81
<211> LENGTH: 39
<212> TYPE: DNA
<213> ORGANISM: Artificial Sequence
<220> FEATURE:
<223> OTHER INFORMATION: Synthetic Construct

<400> SEQUENCE: 81
atcactcatg gttatggcag cactgcataa ttctcttac                             39

<210> SEQ ID NO 82
<211> LENGTH: 39
<212> TYPE: DNA
<213> ORGANISM: Artificial Sequence
<220> FEATURE:
<223> OTHER INFORMATION: Synthetic Construct

<400> SEQUENCE: 82
gtaagagaat tatgcagtgc tgccataacc atgagtgat                             39
```

<210> SEQ ID NO 83
<211> LENGTH: 57
<212> TYPE: DNA
<213> ORGANISM: Artificial Sequence
<220> FEATURE:
<223> OTHER INFORMATION: Synthetic Construct

<400> SEQUENCE: 83
gtttgccgga tcgtcgacca tacttactaa tcacgatagg gatgaatcgt tttaatt    57

<210> SEQ ID NO 84
<211> LENGTH: 57
<212> TYPE: DNA
<213> ORGANISM: Artificial Sequence
<220> FEATURE:
<223> OTHER INFORMATION: Synthetic Construct

<400> SEQUENCE: 84
aattaaaacg attcatccct atcgtgatta gtaagtatgg tcgacgatcc ggcaaac    57

<210> SEQ ID NO 85
<211> LENGTH: 54
<212> TYPE: DNA
<213> ORGANISM: Artificial Sequence
<220> FEATURE:
<223> OTHER INFORMATION: Synthetic Construct

<400> SEQUENCE: 85
gataaccgta accgaagatg ataactgaca agggcagaaa gtcaaaagcc tccg    54

<210> SEQ ID NO 86
<211> LENGTH: 54
<212> TYPE: DNA
<213> ORGANISM: Artificial Sequence
<220> FEATURE:
<223> OTHER INFORMATION: Synthetic Construct

<400> SEQUENCE: 86
cggaggcttt tgactttctg cccttgtcag ttatcatctt cggttacggt tatc    54

<210> SEQ ID NO 87
<211> LENGTH: 40
<212> TYPE: DNA
<213> ORGANISM: Artificial Sequence
<220> FEATURE:
<223> OTHER INFORMATION: Synthetic Construct

<400> SEQUENCE: 87
agctaaagat ctagcaagag gaaaaaaaaa tgactatgac    40

<210> SEQ ID NO 88
<211> LENGTH: 23
<212> TYPE: DNA
<213> ORGANISM: Artificial Sequence
<220> FEATURE:
<223> OTHER INFORMATION: Synthetic Construct

<400> SEQUENCE: 88
ctcgagtaag gatctccagg cat    23

<210> SEQ ID NO 89
<211> LENGTH: 23
<212> TYPE: DNA
<213> ORGANISM: Artificial Sequence
<220> FEATURE:

<223> OTHER INFORMATION: Synthetic Construct

<400> SEQUENCE: 89
atgcctggag atccttactc gag                                              23

<210> SEQ ID NO 90
<211> LENGTH: 49
<212> TYPE: DNA
<213> ORGANISM: Artificial Sequence
<220> FEATURE:
<223> OTHER INFORMATION: Synthetic Construct

<400> SEQUENCE: 90
gtttgccgga tcgtcgacca tacttattag gggcaggcga cgtcttttc                  49

<210> SEQ ID NO 91
<211> LENGTH: 49
<212> TYPE: DNA
<213> ORGANISM: Artificial Sequence
<220> FEATURE:
<223> OTHER INFORMATION: Synthetic Construct

<400> SEQUENCE: 91
gaaaagacgt cgcctgcccc taataagtat ggtcgacgat ccggcaaac                  49

<210> SEQ ID NO 92
<211> LENGTH: 48
<212> TYPE: DNA
<213> ORGANISM: Artificial Sequence
<220> FEATURE:
<223> OTHER INFORMATION: Synthetic Construct

<400> SEQUENCE: 92
tatatctcga gattggatcc ttatgagtca tgatttacta aaggctgc                   48

<210> SEQ ID NO 93
<211> LENGTH: 42
<212> TYPE: DNA
<213> ORGANISM: Artificial Sequence
<220> FEATURE:
<223> OTHER INFORMATION: Synthetic Construct

<400> SEQUENCE: 93
tttttcgaat tcaccagatc tctgcagtag gaggaattaa cc                         42

<210> SEQ ID NO 94
<211> LENGTH: 42
<212> TYPE: DNA
<213> ORGANISM: Artificial Sequence
<220> FEATURE:
<223> OTHER INFORMATION: Synthetic Construct

<400> SEQUENCE: 94
atatttctcg agattggatc cttagaaagc gctcaggaag ag                         42

<210> SEQ ID NO 95
<211> LENGTH: 39
<212> TYPE: DNA
<213> ORGANISM: Artificial Sequence
<220> FEATURE:
<223> OTHER INFORMATION: Synthetic Construct

<400> SEQUENCE: 95
tatagaattc accagatcta attcaaagga ggccatcct                             39

```
<210> SEQ ID NO 96
<211> LENGTH: 43
<212> TYPE: DNA
<213> ORGANISM: Artificial Sequence
<220> FEATURE:
<223> OTHER INFORMATION: Synthetic Construct

<400> SEQUENCE: 96
tatagaattc accagatctg agaggcttta cactttatgc ttc                    43

<210> SEQ ID NO 97
<211> LENGTH: 45
<212> TYPE: DNA
<213> ORGANISM: Artificial Sequence
<220> FEATURE:
<223> OTHER INFORMATION: Synthetic Construct

<400> SEQUENCE: 97
ttaactcgag attggatcct tcctttgaat tcaattgtta tccgc                  45

<210> SEQ ID NO 98
<211> LENGTH: 47
<212> TYPE: DNA
<213> ORGANISM: Artificial Sequence
<220> FEATURE:
<223> OTHER INFORMATION: Synthetic Construct

<400> SEQUENCE: 98
ttaactcgag attggatcct taattggctg ttttaatatc ttcctgc                47

<210> SEQ ID NO 99
<211> LENGTH: 43
<212> TYPE: DNA
<213> ORGANISM: Artificial Sequence
<220> FEATURE:
<223> OTHER INFORMATION: Synthetic Construct

<400> SEQUENCE: 99
tatagaattc accagatcta ctagtaagga ggaaacagaa tgc                    43

<210> SEQ ID NO 100
<211> LENGTH: 69
<212> TYPE: DNA
<213> ORGANISM: Artificial Sequence
<220> FEATURE:
<223> OTHER INFORMATION: Synthetic Construct

<400> SEQUENCE: 100
atccactaca accatatcat cacaagtggt cagacctcct acaagtaagg attccgggga  60
tccgtcgac                                                         69

<210> SEQ ID NO 101
<211> LENGTH: 70
<212> TYPE: DNA
<213> ORGANISM: Artificial Sequence
<220> FEATURE:
<223> OTHER INFORMATION: Synthetic Construct

<400> SEQUENCE: 101
aataattagc ggataaagaa acggagcctt tcggctccgt tattcattta gtgtaggctg  60
gagctgcttc                                                        70

<210> SEQ ID NO 102
<211> LENGTH: 59
<212> TYPE: DNA
```

<213> ORGANISM: Artificial Sequence
<220> FEATURE:
<223> OTHER INFORMATION: Synthetic Construct

<400> SEQUENCE: 102
attaatacgc gagttaagga gtacaggagc atgaaggtga ccaatcagaa agaactgaa        59

<210> SEQ ID NO 103
<211> LENGTH: 60
<212> TYPE: DNA
<213> ORGANISM: Artificial Sequence
<220> FEATURE:
<223> OTHER INFORMATION: Synthetic Construct

<400> SEQUENCE: 103
tactccttaa ctcgcgtatt aatttggatc cttattttga ataatcgtag aaaccttttc       60

<210> SEQ ID NO 104
<211> LENGTH: 50
<212> TYPE: DNA
<213> ORGANISM: Artificial Sequence
<220> FEATURE:
<223> OTHER INFORMATION: Synthetic Construct

<400> SEQUENCE: 104
atctacatta agagcttttg aagatctgaa gcttgggccc gaacaaaaac        50

<210> SEQ ID NO 105
<211> LENGTH: 50
<212> TYPE: DNA
<213> ORGANISM: Artificial Sequence
<220> FEATURE:
<223> OTHER INFORMATION: Synthetic Construct

<400> SEQUENCE: 105 gttttttgttc gggcccaagc ttcagatctt caaaagctct taatgtagat        50

<210> SEQ ID NO 106
<211> LENGTH: 50
<212> TYPE: DNA
<213> ORGANISM: Artificial Sequence
<220> FEATURE:
<223> OTHER INFORMATION: Synthetic Construct

<400> SEQUENCE: 106
ttgtgagcgg ataacaattt cacaccagca ggacgcactg agggcccatg        50

<210> SEQ ID NO 107
<211> LENGTH: 50
<212> TYPE: DNA
<213> ORGANISM: Artificial Sequence
<220> FEATURE:
<223> OTHER INFORMATION: Synthetic Construct

<400> SEQUENCE: 107
catgggccct cagtgcgtcc tgctggtgtg aaattgttat ccgctcacaa        50

<210> SEQ ID NO 108
<211> LENGTH: 58
<212> TYPE: DNA
<213> ORGANISM: Artificial Sequence
<220> FEATURE:
<223> OTHER INFORMATION: Synthetic Construct

<400> SEQUENCE: 108
tttctacgat tattcaaaat aaggatcccg actgcacggt gcaccaatgc ttctggcg       58

<210> SEQ ID NO 109
<211> LENGTH: 60
<212> TYPE: DNA
<213> ORGANISM: Artificial Sequence
<220> FEATURE:
<223> OTHER INFORMATION: Synthetic Construct

<400> SEQUENCE: 109
acctacctcc ttatttcaat tttttcgatg aattgttatc cgctcacaat tccacacatt    60

<210> SEQ ID NO 110
<211> LENGTH: 59
<212> TYPE: DNA
<213> ORGANISM: Artificial Sequence
<220> FEATURE:
<223> OTHER INFORMATION: Synthetic Construct

<400> SEQUENCE: 110
aaaattgaaa taaggaggta ggtagtaatg aaaaattgtg tcatcgtcag tgcggtacg     59

<210> SEQ ID NO 111
<211> LENGTH: 58
<212> TYPE: DNA
<213> ORGANISM: Artificial Sequence
<220> FEATURE:
<223> OTHER INFORMATION: Synthetic Construct

<400> SEQUENCE: 111
tgtactcctt aactcgcgta ttaatttgtt aattcaaccg ttcaatcacc atcgcaat      58

<210> SEQ ID NO 112
<211> LENGTH: 60
<212> TYPE: DNA
<213> ORGANISM: Artificial Sequence
<220> FEATURE:
<223> OTHER INFORMATION: Synthetic Construct

<400> SEQUENCE: 112
gccgtttatg ttgccagaca gcgctactga gtgtaggctg gagctgcttc gaagttccta    60

<210> SEQ ID NO 113
<211> LENGTH: 50
<212> TYPE: DNA
<213> ORGANISM: Artificial Sequence
<220> FEATURE:
<223> OTHER INFORMATION: Synthetic Construct

<400> SEQUENCE: 113
acattatcag gagagcatta ctgtcaaaca tgagaattaa ttccggggat                50

<210> SEQ ID NO 114
<211> LENGTH: 49
<212> TYPE: DNA
<213> ORGANISM: Artificial Sequence
<220> FEATURE:
<223> OTHER INFORMATION: Synthetic Construct

<400> SEQUENCE: 114
ccggaattca aaagatctta ggaggaatat aaaatgaaaa attgtgtca                 49

<210> SEQ ID NO 115
<211> LENGTH: 44
<212> TYPE: DNA
<213> ORGANISM: Artificial Sequence
<220> FEATURE:

<223> OTHER INFORMATION: Synthetic Construct

<400> SEQUENCE: 115
ccgctcgagt ttggatcctc aattcaaccg ttcaatcacc atcg                            44

<210> SEQ ID NO 116
<211> LENGTH: 60
<212> TYPE: DNA
<213> ORGANISM: Artificial Sequence
<220> FEATURE:
<223> OTHER INFORMATION: Synthetic Construct

<400> SEQUENCE: 116
ccggaattca aaagatcttg aattaaggag gacagctaaa tgaaactctc aactaaactt          60

<210> SEQ ID NO 117
<211> LENGTH: 46
<212> TYPE: DNA
<213> ORGANISM: Artificial Sequence
<220> FEATURE:
<223> OTHER INFORMATION: Synthetic Construct

<400> SEQUENCE: 117
ccgctcgagt ttggatcctc attttttaac atcgtaggat cttcta                         46

<210> SEQ ID NO 118
<211> LENGTH: 60
<212> TYPE: DNA
<213> ORGANISM: Artificial Sequence
<220> FEATURE:
<223> OTHER INFORMATION: Synthetic Construct

<400> SEQUENCE: 118
ccggaattca aaagatctaa aataaggagg attacactat ggttttaacc aataaaacag          60

<210> SEQ ID NO 119
<211> LENGTH: 40
<212> TYPE: DNA
<213> ORGANISM: Artificial Sequence
<220> FEATURE:
<223> OTHER INFORMATION: Synthetic Construct

<400> SEQUENCE: 119
ccgctcgagt ttggatcctc aggatttaat gcaggtgacg                                40

<210> SEQ ID NO 120
<211> LENGTH: 60
<212> TYPE: DNA
<213> ORGANISM: Artificial Sequence
<220> FEATURE:
<223> OTHER INFORMATION: Synthetic Construct

<400> SEQUENCE: 120
ccggaattca aaagatctag gaggttaatt ggatgtcatt accgttctta acttctgcac          60

<210> SEQ ID NO 121
<211> LENGTH: 48
<212> TYPE: DNA
<213> ORGANISM: Artificial Sequence
<220> FEATURE:
<223> OTHER INFORMATION: Synthetic Construct

<400> SEQUENCE: 121
ccgctcgagt ttggatccct atgaagtcca tggtaaattc gtgtttcc                       48

```
<210> SEQ ID NO 122
<211> LENGTH: 60
<212> TYPE: DNA
<213> ORGANISM: Artificial Sequence
<220> FEATURE:
<223> OTHER INFORMATION: Synthetic Construct

<400> SEQUENCE: 122
ccggaattca aaagatctta aggaggatac cctatgtcag agttgagagc cttcagtgcc    60

<210> SEQ ID NO 123
<211> LENGTH: 45
<212> TYPE: DNA
<213> ORGANISM: Artificial Sequence
<220> FEATURE:
<223> OTHER INFORMATION: Synthetic Construct

<400> SEQUENCE: 123
ccgctcgagt ttggatccct atttatcaag ataagtttcc ggatc    45

<210> SEQ ID NO 124
<211> LENGTH: 60
<212> TYPE: DNA
<213> ORGANISM: Artificial Sequence
<220> FEATURE:
<223> OTHER INFORMATION: Synthetic Construct

<400> SEQUENCE: 124
ccggaattca aaagatctag gaggattatg agatgaccgt ttacacagca tccgttaccg    60

<210> SEQ ID NO 125
<211> LENGTH: 46
<212> TYPE: DNA
<213> ORGANISM: Artificial Sequence
<220> FEATURE:
<223> OTHER INFORMATION: Synthetic Construct

<400> SEQUENCE: 125
ccgctcgagt ttggatcctt attcctttgg tagaccagtc tttgcg    46

<210> SEQ ID NO 126
<211> LENGTH: 59
<212> TYPE: DNA
<213> ORGANISM: Artificial Sequence
<220> FEATURE:
<223> OTHER INFORMATION: Synthetic Construct

<400> SEQUENCE: 126
ccggaattca aaagatctag gaggtaatga taatgcaaac ggaacacgtc attttattg    59

<210> SEQ ID NO 127
<211> LENGTH: 47
<212> TYPE: DNA
<213> ORGANISM: Artificial Sequence
<220> FEATURE:
<223> OTHER INFORMATION: Synthetic Construct

<400> SEQUENCE: 127
ccgctcgagt ttggatcctt atttaagctg ggtaaatgca gataatc    47

<210> SEQ ID NO 128
<211> LENGTH: 28
<212> TYPE: DNA
<213> ORGANISM: Artificial Sequence
<220> FEATURE:
<223> OTHER INFORMATION: Synthetic Construct
```

```
<400> SEQUENCE: 128
cccgggttaa ttctgacgaa atgccacg                                              28

<210> SEQ ID NO 129
<211> LENGTH: 26
<212> TYPE: DNA
<213> ORGANISM: Artificial Sequence
<220> FEATURE:
<223> OTHER INFORMATION: Synthetic Construct

<400> SEQUENCE: 129
ccatggaatt tgacttcaac aaatac                                                26

<210> SEQ ID NO 130
<211> LENGTH: 27
<212> TYPE: DNA
<213> ORGANISM: Artificial Sequence
<220> FEATURE:
<223> OTHER INFORMATION: Synthetic Construct

<400> SEQUENCE: 130
ccatggcgcg tcgtatcgcg ggtcacc                                               27

<210> SEQ ID NO 131
<211> LENGTH: 25
<212> TYPE: DNA
<213> ORGANISM: Artificial Sequence
<220> FEATURE:
<223> OTHER INFORMATION: Synthetic Construct

<400> SEQUENCE: 131
cccgggttac agcggaacgg tttca                                                 25

<210> SEQ ID NO 132
<211> LENGTH: 17
<212> TYPE: DNA
<213> ORGANISM: Artificial Sequence
<220> FEATURE:
<223> OTHER INFORMATION: Synthetic Construct

<400> SEQUENCE: 132
ccgccaaaac agccaag                                                          17

<210> SEQ ID NO 133
<211> LENGTH: 41
<212> TYPE: DNA
<213> ORGANISM: Artificial Sequence
<220> FEATURE:
<223> OTHER INFORMATION: Synthetic Construct

<400> SEQUENCE: 133
ccgctgtaac ccggggatcc aattgtgagc ggataacaat t                               41

<210> SEQ ID NO 134
<211> LENGTH: 20
<212> TYPE: DNA
<213> ORGANISM: Artificial Sequence
<220> FEATURE:
<223> OTHER INFORMATION: Synthetic Construct

<400> SEQUENCE: 134
gtccgcacgt ttacggtaag                                                       20

<210> SEQ ID NO 135
<211> LENGTH: 38
```

```
<212> TYPE: DNA
<213> ORGANISM: Artificial Sequence
<220> FEATURE:
<223> OTHER INFORMATION: Synthetic Construct

<400> SEQUENCE: 135
taatccagat cttgacagct tatcatcgac tgcacggt                                38
```